(12) United States Patent
Walters

(10) Patent No.: US 8,865,129 B2
(45) Date of Patent: Oct. 21, 2014

(54) LANTHANOID COMPLEX CAPSULE AND PARTICLE CONTRAST AGENTS, METHODS OF MAKING AND USING THEREOF

(75) Inventor: Marc Anton Walters, New Rochelle, NY (US)

(73) Assignee: New York University, New York, NY (US)

( * ) Notice: Subject to any disclaimer, the term of this patent is extended or adjusted under 35 U.S.C. 154(b) by 29 days.

(21) Appl. No.: 13/464,718

(22) Filed: May 4, 2012

(65) Prior Publication Data

US 2012/0294809 A1    Nov. 22, 2012

Related U.S. Application Data

(60) Provisional application No. 61/482,950, filed on May 5, 2011, provisional application No. 61/604,770, filed on Feb. 29, 2012.

(51) Int. Cl.
| | | |
|---|---|---|
| *A61K 49/00* | (2006.01) | |
| *A61K 49/18* | (2006.01) | |
| *A61K 49/10* | (2006.01) | |
| *A61K 9/51* | (2006.01) | |
| *A61K 49/12* | (2006.01) | |
| *C07D 257/02* | (2006.01) | |

(52) U.S. Cl.
CPC .......... *C07D 257/02* (2013.01); *A61K 49/106* (2013.01); *A61K 49/1809* (2013.01); *C07K 5/003* (2013.01); *A61K 9/5176* (2013.01); *A61K 49/124* (2013.01); *A61K 49/1881* (2013.01)
USPC .......................... 424/9.322; 424/9.1; 424/9.6

(58) Field of Classification Search
USPC ............ 424/9.1, 9.32, 9.6; 540/460, 465, 474
See application file for complete search history.

(56) References Cited

U.S. PATENT DOCUMENTS 5,922,862 A * 7/1999 Murru et al. .................. 540/474

FOREIGN PATENT DOCUMENTS

| WO | 2008134289 A2 | 11/2008 |
|---|---|---|
| WO | 2009123934 A2 | 10/2009 |

OTHER PUBLICATIONS

Delgado et al., "Lanthanide Complexes of Macrocyclic Derivatives Useful for Medical Applications," Pure Appl. Chem., 77(3):569-79 (2005).
Xu et al., "Labeling of Polymer Nanostructures for Medical Imaging: Importance of Cross-Linking Extent, Spacer Length, and Charge Density," Macromolecules, 40(9):2971-73 (2007).
Endres et al., "DNA—TiO2 Nanoconjugates Labeled with Magnetic Resonance Contrast Agent," J. Am. Chem. Soc., 129(51):15760-61 (2007).
Carniato et al., "A Chemical Strategy for the Relaxivity Enhancement of GdIII Chelates Anchored in Mesoporous Silica Nanoparticles," Chem. Eur. J. 16(35):10727-34 (2010).

* cited by examiner

*Primary Examiner* — Michael G Hartley
*Assistant Examiner* — Jagadishwar Samala
(74) *Attorney, Agent, or Firm* — LeClairRyan, a Professional Corporation

(57) ABSTRACT

The invention relates to compositions of DOTA derivative compounds, lanthanoid-DOTA derivative molecular complex, and lanthanoid-complex encapsulated solid lipid particles or capsules, and methods of making and using the compositions. The solid lipid particles or capsules contain micelle cores stabilized by a hyperbranched polymer shell based from a crosslinked DOTA derivative compound or crosslinked lanthanoid-DOTA derivative complex. These solid lipid particles or capsules can be used in various applications, such as contrast agents or drug delivery vehicles.

17 Claims, 7 Drawing Sheets

LANTHANOID COMPLEX CAPSULE AND PARTICLE CONTRAST AGENTS, METHODS OF MAKING AND USING THEREOF

This application claims the benefit of U.S. Provisional Patent Application Ser. No. 61/482,950, filed May 5, 2011 and U.S. Provisional Patent Application Ser. No. 61/604,770, filed Feb. 29, 2012, both of which are hereby incorporated by reference in their entirety.

FIELD OF THE INVENTION

The present invention relates to lanthanoid-complex encapsulated solid lipid nanoparticles, or lanthanoid-complex nanoparticles, methods of making and using thereof.

BACKGROUND OF THE INVENTION

Biomedical imaging, such as magnetic resonance imaging (MRI), is a compelling imaging method as it allows peering into body with non-ionizing radiation. The images thus acquired enable the diagnosis and treatment of conditions that were previously revealed only by the scalpel. Generating new nanoscale imaging agents that can provide precise and high contrast views of lesions that would guide focused and effective treatment is certainly going to benefit biomedical imaging.

Multimodal nanoparticles are great vehicles with which to achieve simultaneous targeting, imaging, and drug delivery, an important goal in modern pharmacology (BHANU P. S. CHAUHAN: HYBRID NANOMATERIALS: SYNTHESIS, CHARACTERIZATION, AND APPLICATIONS, (John Wiley & Sons, Hoboken, N.J., 2011)). As part of this effort, an MRI imaging agent comprised of gadolinium complexes has recently been assembled on the surface of silver nanoparticles (Siddiqui et al., *J. Colloid Interf. Sci.* 337:88 (2009)). Noble metal NPs have been used in the development of multifunctional agents for the diagnosis and/or treatment of disease, because noble nanoparticles such as gold and silver nanoparticles are easy to synthesize. Such particles can be made multifunctional by supporting moieties anchored on their surface.

However, certain drawbacks exist in the use of noble metal particles for routine clinical use. For instance, these particles are expensive, and the use of these particles is inefficient because of an unused interior volume. Moreover, metal particles above 5-8 nm diameters are cleared only slowly through a hepatic pathway.

Solid lipid nanoparticles (SLNs) offer an important alternative for the formation of multimodal theranostic agents (Lammers et al., *Acc. Chem. Res.* 44(10):1029 (2011); Andreozzi et al., *Bioconjugate Chem.* 22:808 (2011)). They have certain characteristics that suit them for combined drug delivery and diagnostics (Muller et al., *Eur. J. Pharm. Biopharm.* 50:161 (2000)). Gd-containing SLNs has been reported as MRI contrast agents (Morel et al., *Eur. J. Pharm. Biopharm.* 45:157 (1998)). In that report, the uptake of gadolinium diethylenetriamine-N,N,N',N"N"-pentaacetate (GdDTPA) and gadolinium tetraazacyclododecanetetraacetic acid (GdDOTA) to form the contrast agents was described, but the question of the contrast agent's location in relation to the surface of the SLN particle was left open. As a result, the mechanisms of contrast enhancement by Gd-containing SLNs could not be specified. In this type of particle, the subsurface/surface location of the contrast agent determines the degree to which proton spin relaxation of water is due to inner sphere, $T_1$ relaxation (surface) or outer sphere $T_1$ and $T_2$, or susceptibility relaxation (subsurface) (Fossheim et al., *J. Magn. Reson. Imaging* 7:251 (1997)). In a follow-up study, a lipid with a polar GdDTPA headgroup was embedded in an SLN surface with GdDTPA confined to the surface (Zhu et al., *J. Nanosci. Nanotechnol.* 6:996 (2006)). A more recent paper describes the incorporation of the $[GdDTPA]^{2-}$ complex within an SLN core for magnetic resonance colonography. The latter particles were prepared in a miniemulsion in which $[GdDTPA]^{2-}$ was introduced in an aqueous phase that also contained monostearin (Sun et al., *Magn. Reson. Med.* 65:673 (2011)). It has also been described that the incorporation of neutral gadolinium acetylacetonate (GdAcAc) in SLNs, generated by nanotemplate engineering, can be used for crossing the blood brain barrier in neutron capture therapy of brain lesions (Oyewumi & Mumper, *Bioconjugate Chem.* 13:1328 (2002)).

The SLN platform has been found advantageous in the above studies from a clinical perspective because of its nanoscale size, biocompatibility, and biodegradation properties that aid clearance. However, the application of SLNs as imaging agents, possibly combined with drug release as theranostic agents, still has not been well developed.

In the United States, MRI contrast agents employ the DTPA ligand and its derivatives to coordinate the contrast-inducing ion $Gd^{3+}$. DTPA is constructed from a diethylene triamine backbone. One attractive feature of DTPA is the ease with which it can be chemically modified to adjust its pharmacokinetics and biodistribution. However, GdDTPA with a stability constant of $10^{22}$ $M^{-1}$ has a significant toxicological drawback. It has been shown to induce nephrogentic systemic fibrosis (NSF) a condition that is sometimes fatal resulting from the release of $Gd^{3+}$ ions due to renal insufficiency (see Bongartz, *Magn. Reson. Mater. Phy.* 20:57 (2007), which is hereby incorporated by reference in its entirety). GdDOTA is more stable by several orders of magnitude with a stability of constant of $10^{28}$ $M^{-1}$ (see Magerstadt et al., *Magnet. Reson. Med.* 3:808 (1986), which is hereby incorporated by reference in its entirety). What is therefore needed is a GdDOTA-based agent that contains functional groups based on DOTA ligands that enables the compositions to be useful in MRI applications. This invention answers that need.

SUMMARY OF THE INVENTION

One aspect of the present invention relates to a compound of formula (I) or (II):

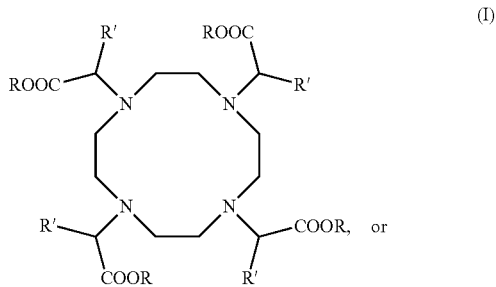

(II)

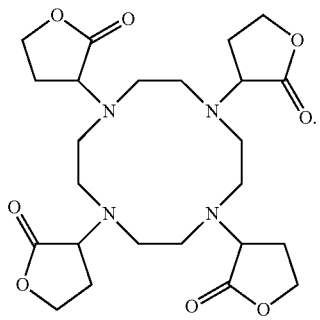

In formula (I) or (II), R is H, alkyl, or a cation; R' is H, or a polymer precursor group which is able to self-crosslink or crosslink in presence of one or more crosslinking agents.

Another aspect of the present invention relates to a molecular complex comprising a molecule of formula (III):

(III)

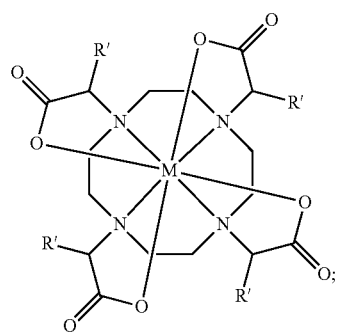

and optionally a balancing counterion. In formula (III), M is a chelated metal ion and R' is H, or a polymer precursor group that is able to self-crosslink or crosslink in presence of one or more crosslinking agents.

Another aspect of the present invention relates to a hyperbranched polymer nanoparticle or nanocapsule comprising hyperbranched polymeric unit having formula (IV):

(IV)

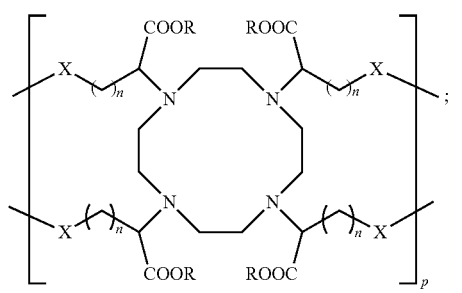

and optionally a crosslinking moiety CL. In formula (IV), R is H, alkyl, or a cation; X is O or S; n is 1-10; p is the number of the units of formula (IV) ranging from 2 to 200,000; and crosslinking moiety CL, if present, is a moiety connecting the hyperbranched polymeric units together through covalently bonding to each X of formula (IV).

Another aspect of the present invention relates to a hyperbranched polymer nanoparticle or nanocapsule comprising a hyperbranched polymeric units having formula (V):

(V)

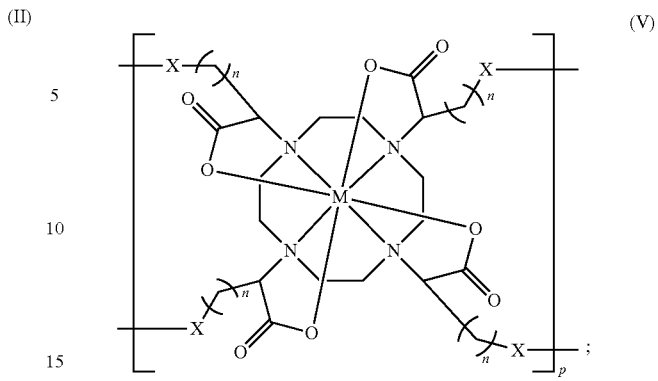

and optionally a crosslinking moiety CL. In formula (V), M is a chelated metal ion; X is O or S; n is 1-10; p is the number of the units of formula (V) ranging from 2 to 200,000; and crosslinking moiety CL, if present, is a moiety connecting the hyperbranched polymeric units together through covalently bonding to each X of formula (V).

A series of DOTA derivative contrast agents have been developed to provide a stable contrast agent while incorporating additional groups that enable modification for enhanced (1) bioavailability, (2) pharmacokinetics, and (3) specificity. In particular, a class of nanoscale MRI contrast agent has been synthesized to provide high contrast of MRI images by assembling contrast-inducing ions in a cluster of sites on hyperbranched polymeric particles. The method employs charge pairing between cationic surfactants and anionic monomers that yield compact polymeric structures with or without the aid of coupling agents. The hyperbranched polymeric particles are formed from metal complexes containing a chelated metal ion, for instance, a lanthanoid such as $Gd^{3+}$ or $Eu^{3+}$, with DOTA or its derivative as the monomer and metal coordination site. The cationic solid lipid nanoparticles were formed with metal-DOTA derivatives complexes as couterions on the surface of the nanoparticles, the pendant hydroxyl groups on metal-DOTA derivative complexes act as precursors for Stern layer polymerization with or without the aid of crosslinking agents.

The synthetic method by which the contrast agents were produced is flexible and allows for the use of molecular groups that target specific tissues, enhance solubility, and shield the agents from the immune system. A large number of modifications can be made on the DOTA-based ligand system by the method described herein to prepare additional new MRI/PET agents.

The hyperbranched polymer-based particles and capsules are multimodal structures that can carry a high concentration of contrast enhancing and imaging agents. They are organic nanostructures that are chemically related to single molecule complexes currently used for biomedical imaging. The compact polymeric nanoparticles are robust and are suitable for biomedical imaging, catalysis, and materials synthesis.

The hyperbranched polymer based particles also allow the incorporation of drugs within the particle core or appending drug molecules to the particle surface: the particles are approximately 5-10 nm in size, small enough for direct clearance through the kidneys, thus are suitable as a drug delivery vehicle.

DETAILED DESCRIPTION OF THE INVENTION

Figure 1:
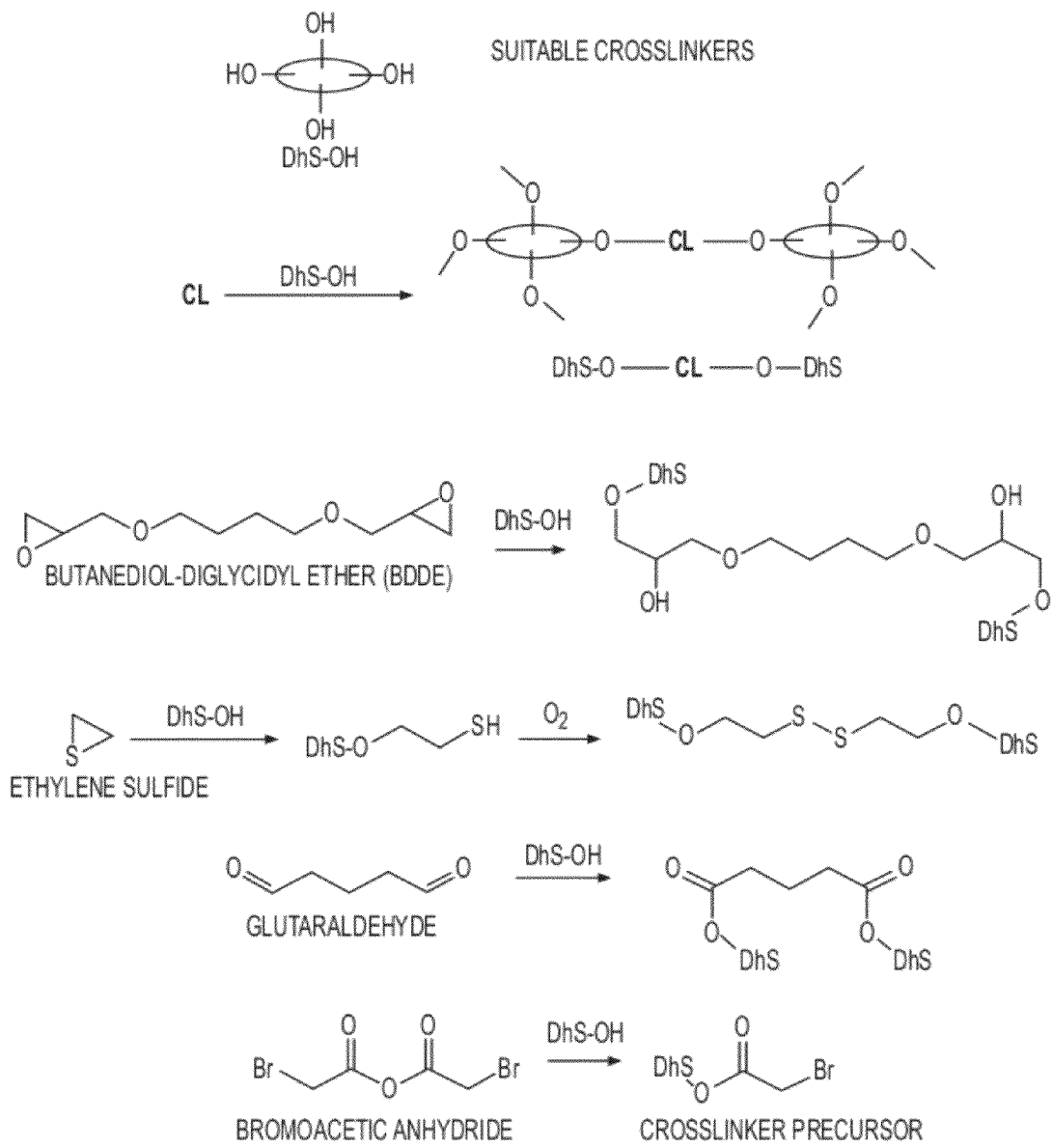
FIG. 1 depicts exemplary crosslinkers and corresponding crosslinking reactions for an exemplary compound DhS-OH. DhS refers to DOTA homoserine.

One aspect of the invention relates to a compound of formula (I) or (II):

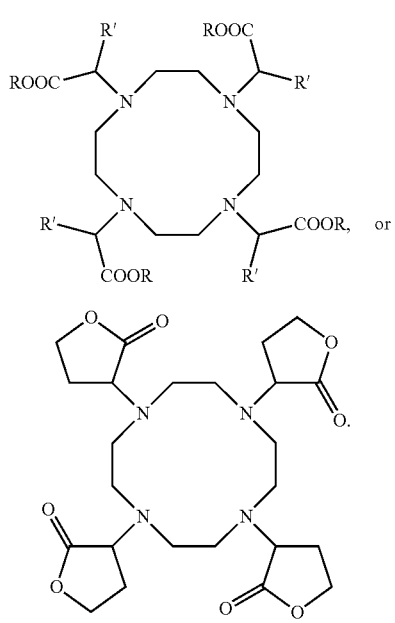

Another aspect of the invention relates to a molecular complex comprising a molecule of formula (III):

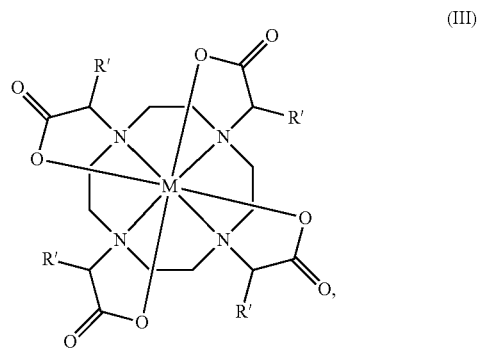

and optionally a balancing counterion.

In formula (I) or (III), R is H, alkyl, or a cation. For instance, R can be H, Li$^+$, Na$^+$, K$^+$, NH$_4^+$, R"NH$_3^+$R"$_2$NH$_2^+$ R"$_3$NH$^+$, where R" can be an alkyl.

R' is H, or a polymer precursor group which is able to self-crosslink or crosslink in presence of one or more crosslinking agents. For instance, R' can be H or a substituted alkyl group. Examples for R' group include hydroxyalkyl, alkylthioalkyl, and mercaptoalkyl or a radical thereof. In one embodiment, R' is —CH$_2$—OH, —C$_2$H$_4$—OH, —C$_2$H$_4$—SH or —C$_2$H$_4$—S—, or —C$_2$H$_4$—S—CH$_3$.

In formula (III), the metal ion M is a chelated metal ion, and can be any metal that can be chelated in the macrocycle structure of formula (III), known to one skilled in the art. For instance, the metal ion M can be a lanthanoid or an 111A atom. Examples for M are La, Eu, Tb, Gd, Ga, and In.

The compounds of formula (I) and (III) are considered 1,4,7,10-tetraazacyclododecane-1,4,7,10-tetraacetic acid (DOTA) or its derivatives. DOTA or its derivatives can be prepared by reacting cyclen, having the chemical formula

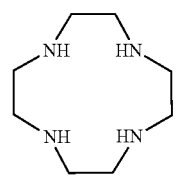 [SMILES: C1CNCCNCCNCCN1]

(1,4,7,10-tetraazacyclododecane) with a precursor compound under conditions effective to provide functional groups as substituents on the N atoms on cyclen. For instance, bromobutyrolactone can be used as a precursor compound that reacts with cyclen under mild conditions (i.e., at atmospheric pressure and room temperature) to add butyrolactone on each N atom on cyclen, resulting in cyclen tetrabutyrolactone (i.e., the compound of formula II). Base hydrolysis of the lactone then produces DOTA homoserine (DhS) (1), as shown in formula (I) where R═—H, R'═—CH$_2$CH$_2$OH. The homoserine hydroxyl group can serve as the site for further derivativization. For instance, the side chains can be modified to produce thiol terminal groups (see Lazar et al., *Eur. J. Org. Chem.* 351 (2002), which is hereby incorporated by reference in its entirety).

The compounds of formula (I) can be either chiral or anchiral.

As shown in Scheme 1, one DOTA derivative is available as an achiral compound, DOTA(homoser)$_4$, (DhS) (1) which is derived from cyclen tetrabutyrolactone (see Lazar et al., *Eur. J. Org. Chem.* 351 (2002), which is hereby incorporated by reference in its entirety).

Two additional compounds DOTA(ser)$_4$, (DS) (2) and DOTA(met)$_4$, (DM) (3) are modifications of DOTA in which the side chains of serine and methionine, respectively, extend from the a carbon of the four acid groups of DOTA (Scheme 1). The products are formed from reactions between cyclen and 2-bromo-3-hydroxypropanoic acid (from serine) and 2-bromo-4-(methylthio)butanoic acid (from methionine), respectively. Both DS and DM are chiral and can be modified at the acidic side chains to modulate their bioavailability, or they can be incorporated into larger structures such as oligomers, polymers, and proteins.

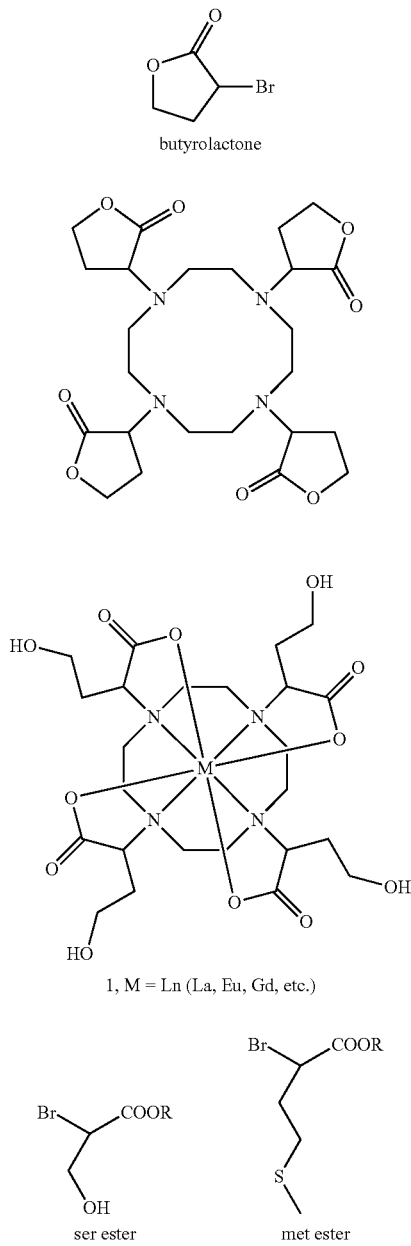

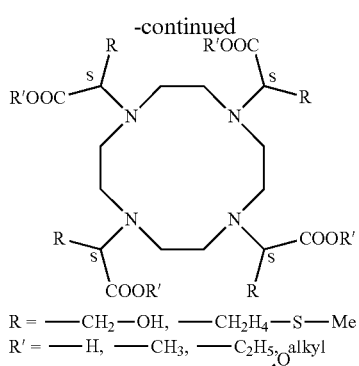

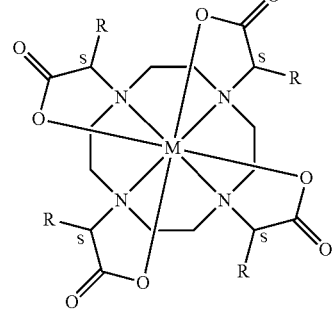

The compounds of formula (I) can be used as complexing agents to chelate ions. In particular, the compound of formula (III) is a molecular complex formed from DOTA derivatives chelating a metal ion M, such as lanthanoids and other metal ions. Such molecular complexes can be used as for biomedical imaging, catalysis, sensors, and materials synthesis. For example, compounds 1 and 2 can be assembled to form nanoparticles through ether or ester bond formation between adjacent DOTA complexes by divinyl sulfone (DVS) or dicarboxylic acids, respectively. Compound 3 can be demethylated at sulfur to form a precursor complex that can be oligomerized through the formation of disulfide bonds. This precursor compound can be employed as a building block for metal-organic-frameworks (MOFs) wherein the thioethers can bond to suitable metals such as $Ag^+$, $Cu^+$ or $Zn^{2+}$.

The chelation structures of formula (III) form eight coordinate tetramino-tetracarboxylato metal complexes. In each resulting complex, four a carbon pendant groups remain available for further derivatization or crosslinking reactions. For instance, the ligands DS, DM, and DhS can incorporate $Ln^{3+}$ ions to produce molecular complexes, e.g., [LnDOTA(ser)$_4$]$^-$.

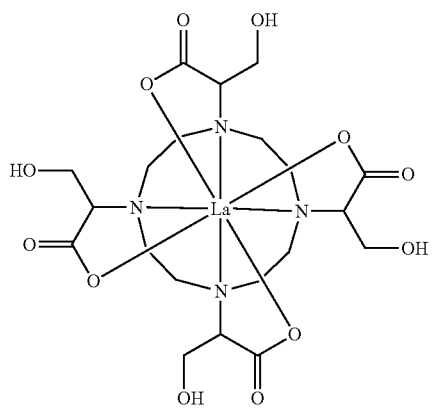

The ligand DhS forms analogous complexes with hydroxy ethyl groups at the α carbon of each of the four carboxylic acids of the ligand. These ligands are precursors for more elaborate molecules with attributes that include high specificity, biocompatibility, desirable pharmacokinetic properties and the like. They are also monomer precursors to hyperbranched polymeric nanoparticles and nanocapsules. The hydroxy groups of DS or DhS can be linked to the same or different adjacent monomers.

The structures of compounds of formula (I) and (II) or molecular complexes of formula (III) obtainable by the above routes can form hyperbranched polymeric capsules, or particles. These particles or capsules can be prepared from homogeneous monomers or prepared by mixing different monomers. They can be used homogeneously or mixed with different components.

An additional aspect of the present invention provides a method of making a hyperbranched polymeric nanoparticle or nanocapsule. The method comprises connecting the compounds of formula (I) or molecular complexes of formula (III) described above through modifying the functional group of R'. The modifications include crosslinking the compounds or molecular complexes described above with their neighboring compounds or molecular complexes through bond formations, such as ether, ester or disulfide bond formations.

In one embodiment, the R' group is hydroxyalkyl. The compound of formula (I) and (II) or molecular complex of formula (III) is bonded to the adjacent compounds or molecular complexes through one or more crosslinking agents.

In one embodiment, the R' group is mercaptoalkyl or radical of mercaptoalkyl. The compound of formula (I) and (II) or molecular complex of formula (III) is bonded to adjacent compounds or molecular complexes through disulfide bond formations. For instance, the R' group can be an alkylthioalkyl, and the connecting step comprises removing the terminal alkyl group of R', and the remaining terminal sulfide is used to form disulfide bonds between compounds or molecular complexes.

Accordingly, one aspect of the invention relates to a hyperbranched polymer nanoparticle or nanocapsule comprising: hyperbranched polymeric units having formula (IV):

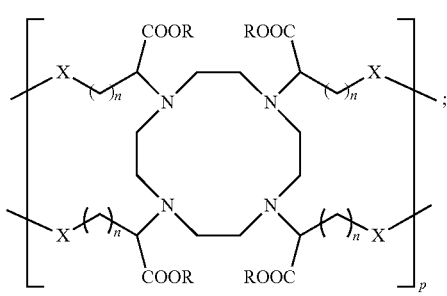

and optionally a crosslinking moiety CL.

Another aspect of the invention relates to a hyperbranched polymer nanoparticle or nanocapsule comprising: hyperbranched polymeric units having formula (V):

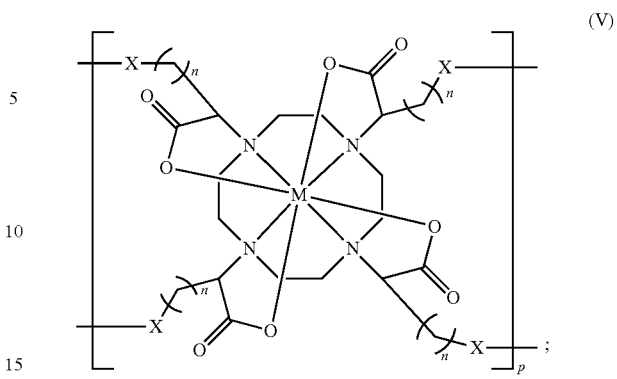

and optionally a crosslinking moiety CL,

In formula (IV) or (V), R is H, alkyl, or a cation. For instance, R can be H, $Li^+$, $Na^+$, $K^+$, $NH_4^+$, $R''NH_3^+R''_2NH_2^+$ $R''_3NH^+$, where R'' can be an alkyl. X is O or S. The variable n is 1-10. For instance, n is 1-6, 1-4 or 1-2. The variable p is the number of the units of formula (IV) or (V) ranging from 2 to 200,000. In one embodiment, p ranges from 10 to 5000, for instance from 20 to 400, for hyperbranched polymer nanoparticle formed from the hyperbranched polymeric units (IV) or (V). In another embodiment, p ranges from 10,000 to 200,000, for instance from 18,000 to 170,000, for hyperbranched polymer nanocapsule formed from the hyperbranched polymeric units (IV) or (V).

The hyperbranched structures form by crosslinking. The crosslinking method is similar to crosslinking copolymer blocks to form micelles. See for example, Read & Armes, *Chem. Comm.* 3021 (2007), which is hereby incorporated by reference in its entirety.

The hyperbranched polymeric units having formula (IV) or (V) are formed by crosslinking the monomeric form, which is compound of formula (I), or (III), in the presence or absence of one or more crosslinking agent. Crosslinking reaction can happen directly by linking the R' groups of the formula with the adjacent compounds or molecular complexes, as described above. Alternatively, the R' groups of the formula can be modified to present functional group that is capable of crosslinking reaction to bond with the R' groups or modified R' groups of the adjacent compounds or molecular complexes.

Methods of modifying R' groups and crosslinking reactions between the R' groups or modified R' groups to form a hyperbranched polymer nanoparticle or nanocapsule are those known to one skilled in the art. For instance, crosslinking reaction can occur through ether or ester, where R' or modified R' has a terminal —OH group, or disulfide bond formations where R' or modified R' has a terminal —SH or —S. group.

Suitable crosslinking agents include, but are not limited to, divinyl sulfone (DVS), dicarboxylic acid, diepoxybutane, diepoxyoctane, divinyladipate (DVA), epichlorohydrin, butanediol-diglycidyl ether (BDDE), ethylene glycol diglycidyl ether, polyglycerol polyglycidyl ether, ethylene sulfide, glutaraldehyde, bromoacetic anhydride, acrylic anhydride, 3-mercaptopropanoate, thioacetic acid, or combinations thereof. Additional descriptions for modifications of R' group and suitable crosslinking reactions/crosslinking agents can be found in Schanté et al., *Carbohydate Polymers* 85:469-89 (2011), which is hereby incorporated by reference in its entirety.

Figure 2:
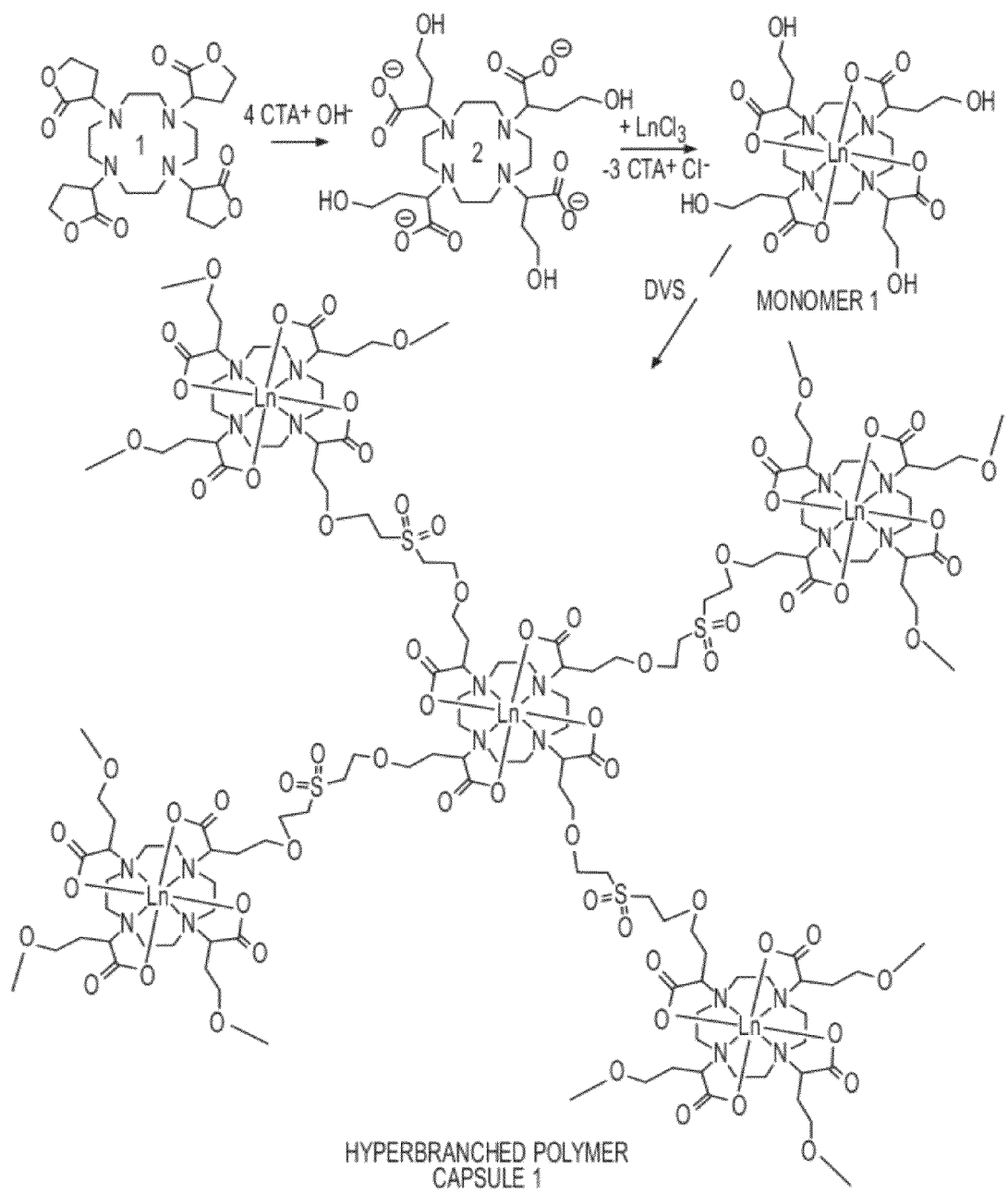
FIG. 2 is a scheme depicting an exemplary process for forming a hyperbraned polymer nanoparticle or nanocapsule.

The crosslinking moiety CL of formula (IV) or (V), if present, is a moiety connecting the hyperbranched polymeric units together through covalently bonding to each X of formula (IV) or (V). Exemplary crosslinking reactions for an exemplary compound DhS-OH including various CLs to form hyperbranched polymeric units are shown in FIG. 1. An exemplary scheme of forming a hyperbraned polymer nanoparticle or nanocapsule is shown in FIG. 2.

One or more catalyst can be used in the crosslinking reaction. For instance, a disulfide forming catalyst, FeNTA, can be used for disulfide formation (Walters et al., *Inorg. Chim. Acta* 359:3996 (2006), which is hereby incorporated by reference in its entirety).

The crosslinking reactions of compounds or molecular complexes of formula (I), (II) or (III) form the hyperbraned polymer shell containing the hyperbranched polymeric unit having the formula (IV) or (V).

In one embodiment, all the terminal groups of all compounds or all molecular complexes of formula (I), (II) or (III), i.e., all four R' groups or modified R' groups, have been crosslinked with R' groups or modified R' groups of neighboring compounds or molecular complexes. Crosslinking compounds or molecular complexes of formula (I), (II) or (III) therefore form a completely enclosed hyperbraned polymer shell showing by the hyperbranched polymeric units of formula (IV) or (V).

In another embodiment, not all terminal groups of all compounds or all molecular complexes of formula (I), (II) or (III) have been crosslinked with the neighboring compounds or molecular complexes. In this regard, the hyperbraned polymer nanoparticle or nanocapsule then contain not only the hyperbranched polymeric units of formula (IV) or (V), but also the terminal compounds or terminal molecular complexes which have terminal functional groups that have not been crosslinked with the neighboring compounds or molecular complexes. These terminal compounds or terminal molecular complexes then can have formula (I), or (III), with one, two or three R' groups crosslinked with the hyperbranched polymeric units of formula (IV) or (V). For instance, in FIG. 2, the hyperbraned polymer capsule 1 contains a hyperbranched polymeric unit that can be represented by formula (V) in the central, and four terminal molecular complexes having formula (III), each of which has one R' group crosslinked with the central hyperbranched polymeric unit and three terminal R' groups that have not been crosslinked with other molecular complexe.

In one embodiment, X is S; formula (IV) or (V) is connected to each other through disulfide bond without the aid of crosslinking agent. Thus formula (IV) or (V) does not contain the crosslinking moiety CL.

In one embodiment, X is O; formula (IV) or (V) is connected to each other with the aid of one or more crosslinking agents.

The metal ion M is in formula (V) is the same as it is defined in formula (III), and has been described above.

For example, lanthanoid complexes of the DOTA derivative DM have four methyl sulfido ethyl groups at the a carbon of the ligand acids. The methyl groups can be removed in sodium/liquid ammonia solution to form DOTA(homocysteine)$_4$, (DhC). Lanthanoid complexes of this ligand, LnDOTA(homocys)$_4$ can be converted to a hyperbranched polymer shell through disulfide bond formation.

Some embodiments of the present invention also provide a hyperbranched polymer shell comprising the crosslinked hyperbranched polymeric nanoparticles or nanocapsules described in the above embodiments.

Another aspect of the present invention relates to a mixed micelle or a solid lipid nanoparticle formed from the mixed micelle. The mixed micelle comprises micelle core, formed by such as an emulsifying wax; and at least one cationic surfactant associated to the surface of the micelle core.

Any surfactants can be used to form the micelle core. Exemplary micelle core is formed from an emulsifying wax; a lipid, such as tricaprin, trimyristin, tripalmitin, tristearin; hydrogenated coco-glycerides; or a hard fat, such as WITEPSOL®, MASSA ESTARINUM®, or Compritol® 888 ATO; a stearic acid; or a soybean lecithin.

Any cationic surfactant known to one skilled in the art for forming solid lipid nanoparticle or nanocapsule can be used to prepare the cationic surfactant associated to the surface of the micelle core. Suitable cations of the cationic surfactant include, but are not limited to, alkyltrimethylammonium such as cetyltrimethylammonium; dimethyldioctadecylammonium; dioctadecyldimethylammonium, etc. Suitable sources of these cations of the cationic surfactant include, but are not limited to, alkyltrimethylammonium salts: such as cetyl trimethylammonium bromide (CTAB) or cetyl trimethylammonium chloride (CTAC); cetylpyridinium chloride (CPC); dimethyldioctadecylammonium chloride; dioctadecyldimethylammonium bromide (DODAB); cetyldimethylammonium acetamide bromide; or other cationic surfactant alike, including lipids.

The anionic portion of the cationic surfactant is the hyperbranched polymeric nanoparticle or nanocapsules described in the above embodiments.

The mixed micelle may further comprise at least one neutral surfactant. The molecular chains of this neutral surfactant can intersperse the individual molecules of cationic surfactant. For instance, the neutral surfactant can be a polyethelene glycol lauryl ether. In one embodiment, the neutral surfactant is Brij L23, which is a PEG-containing diblock copolymer surfactant.

The SLNs formed herein are enclosed, or at least partially enclosed, by the hyperbranched shell. In an exemplary embodiment, the particle or capsule described herein imbed cationic surfactants such as CTAB or CTAC, and neutral surfactants such as Brij surfactant in the SLN surface and then exchange Br of CTAB or Cl of CTAC with [MDOTA]$^-$. The introduction of DVS as a linker monomer leads to the formation of a hyperbranched—{[LnDOTA]$^-$-DVS}$_n$—shell above the SLN and nestled below the polyether arms of Brij L23 that extend outward from the surface of the SLN. See FIGS. 3A-3B. The polyether arms confer water solubility on the particle and serve as a steric barrier to inter-particle crosslinking.

The hyperbranched shell encapsulating SLNs can have a dispersed size range, from 5 nm to 500 nm. In one embodiment, the average size of the nanoparticle or nanocapsule ranges from about 50 to about 150 nm.

Another aspect of the present invention relates to a method of preparing a mixed micelle or a solid lipid nanoparticle formed from a mixed micelle. The method comprises formulating a micelle core by mixing an emulsifying wax, at least one neutral surfactant, and at least one cationic surfactant, wherein the anionic portion of the cationic surfactant is the molecular complex of formula (I) or (III); crosslinking the molecular complexes by modifying the functional group of R', optionally bonded through one or more crosslinking agents, to form a hyperbranched polymeric shell around the micelle core, thereby forming a solid lipid nanoparticle. The hyperbraned polymeric shell around the micelle core contains the hyperbranched polymeric unit having the formula (IV) or (V), and has been described above.

When large particles or aggregates are present when formulating the mixed micelle, the reaction mixture can be filtered before the crosslinking step to remove these large particles or aggregates.

The micelle core, neutral surfactant, and anionic portion and cationic portion of the cationic surfactant have been described in the embodiments above. In one embodiment, the cationic portion of the cationic surfactant is cetyltrimethylammonium, the anionic portion of the cationic surfactant is a hyperbranched polymer shell formed from molecular complex of formula (I) or (III), wherein the metal is a lanthanoid, and the neutral surfactant is polyethelene glycol lauryl ether.

In an exemplary embodiment, when base hydrolysis was carried out with cetyltrimethylammonium hydroxide ($CTA^+$ $OH^-$), the addition of $LnCl_3$ results in a monoanionic lanthanide complex $[LnDhS]^-$ with CTA as its counterion (Scheme 2) as a precursor for capsule assembly.

Scheme 2. $CTA^+[Eu(DOTA-N, N', N'', N'''-tetrahomoserine)]$, CTA [EuDhS]

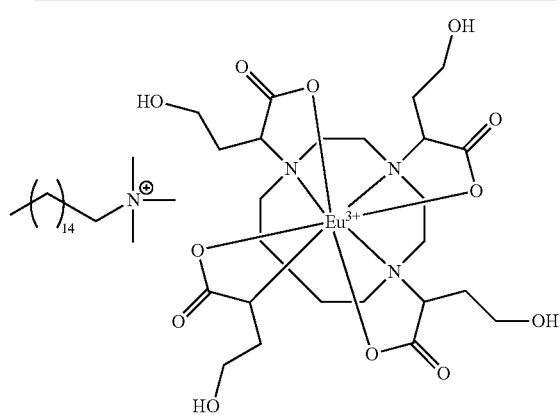

Figure 3A:
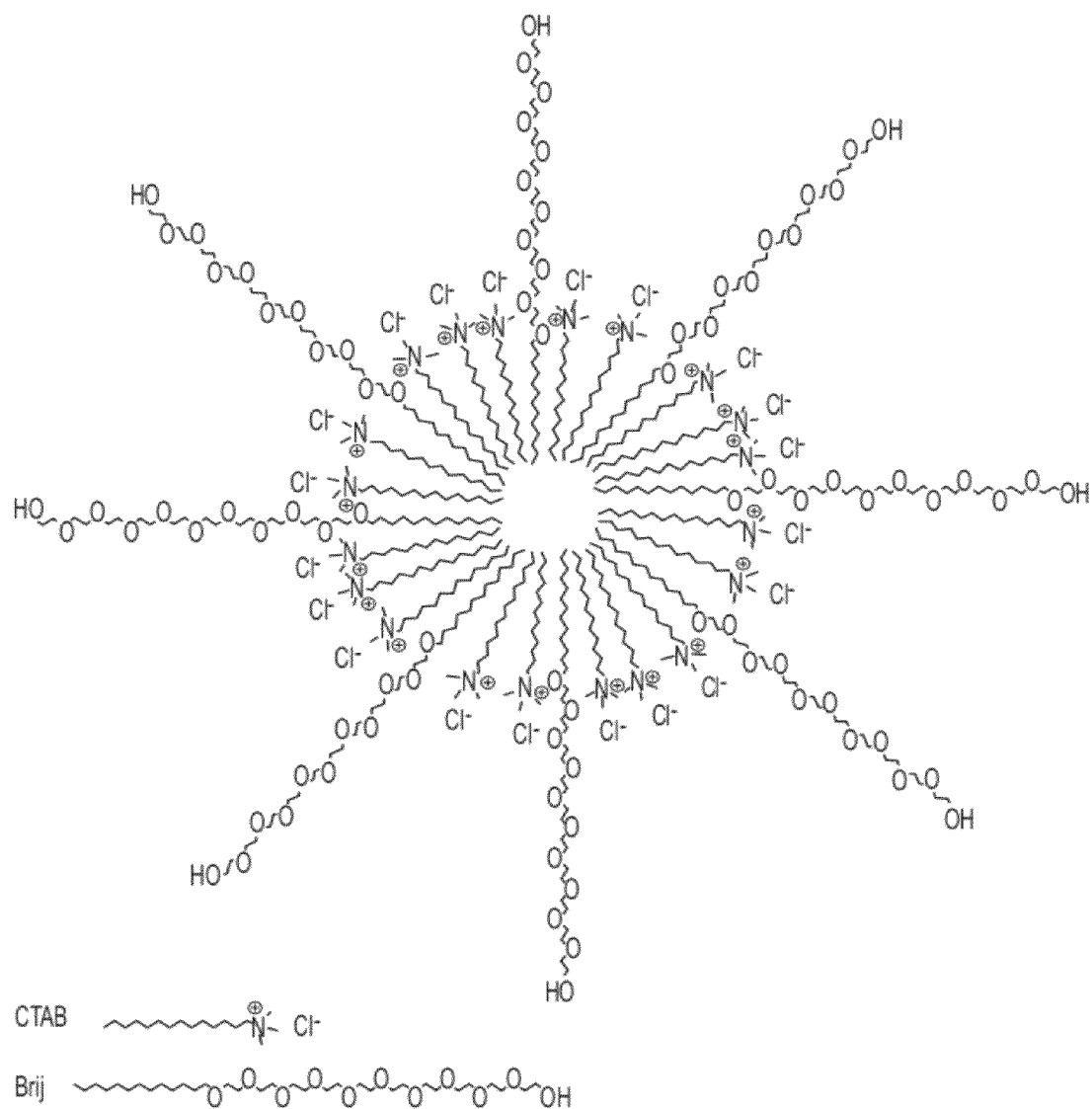
FIG. 3A is a simplified scheme depicting a mixed micelle stabilized by combining the cationic surfactant cetyltrimethylammonium chloride (CTAC) with the neutral surfactant polyethylene glycol lauryl ether (Brij 35) on its surface.

The mixed micelles can be stabilized by combining the cationic surfactant cetyltrimethylammonium bromide (CTAB) with the neutral surfactant polyethylene glycol (23) lauryl ether (Brij 35) (FIG. 3A). The replacement of bromide anion with two or more reactive functional groups allows for the preparation of anionic polymers below the coronal (terminal block) region of mixed micelles. An additional description for forming mixed micelle from surfactant can be found in Gao et al., *J. Colloid Interf. Sci.* 273:626 (2004), which is hereby incorporated by reference in its entirety.

Figure 3B:
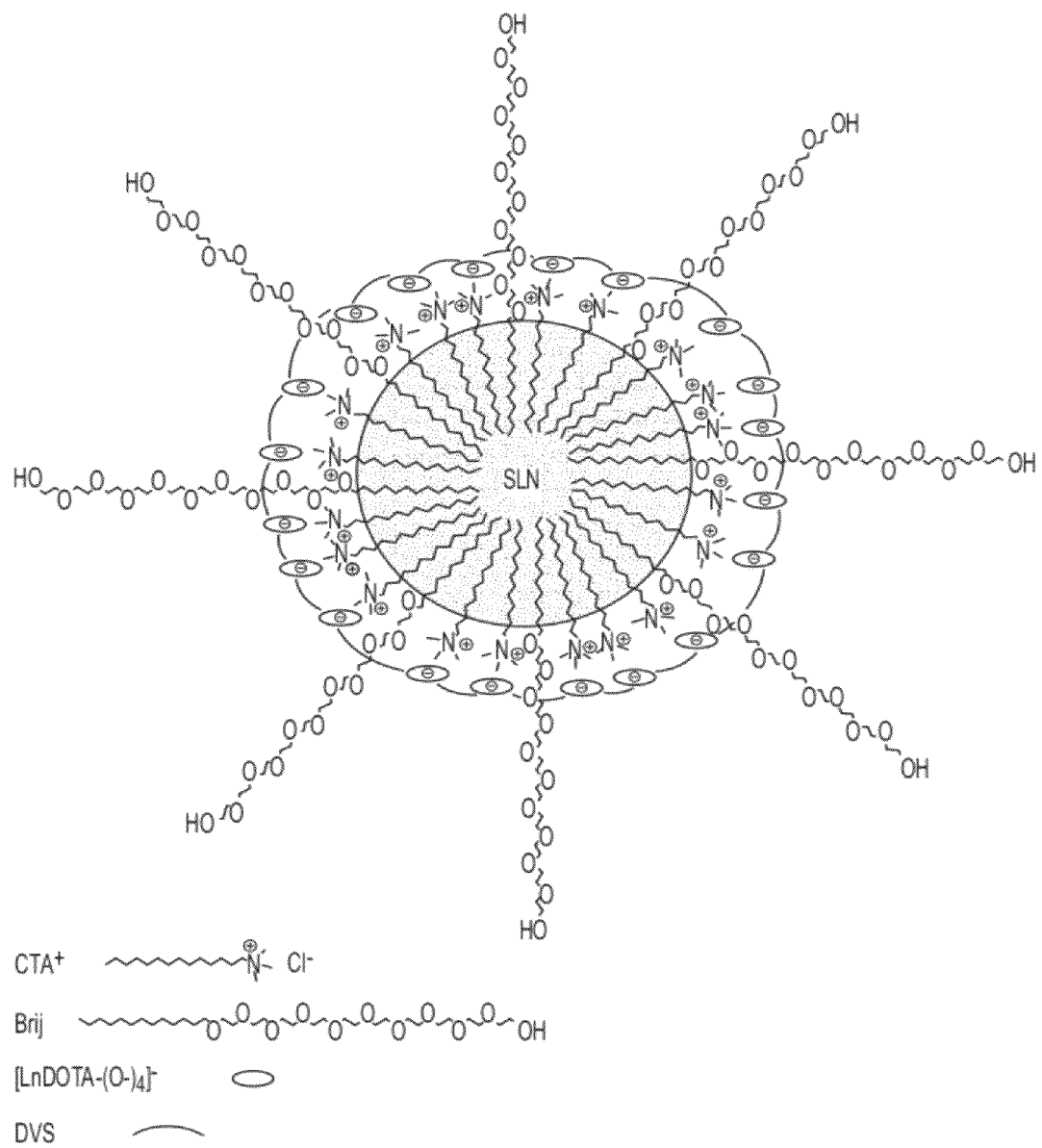
FIG. 3B depicts the detail of hyperbranched polymeric capsule assembly (solid lipid nanoparticle) comprising a mixed micelle core surrounded by a hyperbranched polymeric shell after crosslinking [LnDhS]⁻ of the cationic surfactant with a crosslinking agent, DVS.

The substitution of DS or DhS (monomer A) for the Br ion of CTAB or the $Cl^-$ of CTAC in the Gao-type mixed micelles, and the introduction of DVS (monomer B) as a crosslinker allows the formation of hyperbranched AB polymer networks. In the initial mixed micelle, there is a shell of anions that are closely spaced within the micelle core and therefore distal to adjacent micelles, as enforced by the polyethyl ether chain of Brij 35. The neutral crosslinker induces polymerization in the annular region of the micelle where the anionic groups are paired with the cationic headgroups of CTA (FIG. 3B).

The formation of core-crosslinked micelles can be prepared with di- and tri-block copolymers where one of the blocks has polar hydroxyl groups that form a region suited to accept polar monomers and/or crosslinkers (see Read & Armes, *Chem. Comm.* 3021 (2007); Liu et al., *Langmuir* 18:7780 (2002); Gao et al., *Chem. Mater.* 20:3063 (2008), which are hereby incorporated by reference in their entirety). In the Gao-type mixed micelle, the polar region is the site of the surfactant headgroup. Thus the polar region is explicitly ionic and suited for the introduction of charged monomers or crosslinkers. The specific assembly of anionic polymers in mixed micelles is enabled by (1) the hydrophobicity of the hexadecyl alkane tail of the CTA surfactant, the dodecayl tail of Brij 35 which form the micelle core, (2) the charge pairing of the DOTA anions with the cationic trimethyl ammonium head group of CTA, and (3) the stabilization of the CTA DOTA system by interspersed uncharged surfactants, Brij 35, that sterically prevents the crosslinking between adjacent micelles. The surfactant monomer charge pairing occurs within the recessed regions of the micelle. In sum, the system segregates the anions in an intermediate region of the micelle by the combined effects of CTA micelle formation, charge pairing, and the diblock characteristics of Brij 35 that stabilizes the hydrophobic core and sterically isolates the annular ionic region of the micelle.

Shell formation from the crosslinking of DOTA complexes generates stabilized micelles because the DOTA is simultaneously locked in place by charge pairing with anions in the shell and the Brij surfactant is observed to remain in the structure, yielding a water soluble particle. After the solid lipid nanoparticles are formed and the hyperbranched polymeric shells are formed around the micelle core, the neutral surfactant can be removed from the solid lipid nanoparticle by a solvent. For instance, Brij may be removed with the appropriate solvent, which leaves a hydrophobic crosslinked shell.

Crosslinking between functional groups of monomers leads to stable micelle formation without inter-micelle crosslinking to form undesirable particle dimers, trimers, or clusters. The process may be described as emulsion surface polymerization (ESP). Through ESP, a large variety of anionic compounds can be employed for analogous capsule formation on SLNs, liposomes, other nanoparticles or surfaces.

This synthetic approach can be applied to the vast array of anionic monomers and can be of great commercial importance in the assembly of diagnostic, theranostic, or catalytic nanoparticles. Synthesis of polymers within simple mixed micelles is cost effective and could have limitless applications.

Mixed micelled components can also form a reverse micelle. In one embodiment, the reverse micelles contain the cationic surfactant, such as cetyldimethylammonium acetamide (CDA):

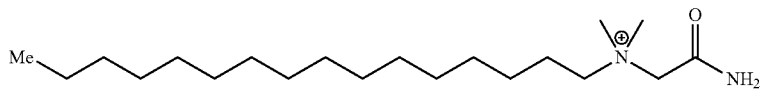 [SMILES: CCCCCCCCCCCCCCCC[N+](C)(C)CC(N)=O]

$[Fe(CN)_6]^{3-}$ (see Walters et al., *Inorg. Chem.* 44:1172 (2005); Mehltretter, *J. Am. Oil Chem. Soc.* 44:219 (1967), both of which are hereby incorporated by reference in their entirety). In this embodiment, $CDA^+$ is employed to form the salt $CDA_4$-[DhS] (see Scheme 2 for a similar structural representation of $CDA_4$-[DhS], wherein $CDA^+$ replaces $CTA^+$). The CDA$_4$-[DhS] salt dissolves in organic solvents to form a microemulsion composed of reverse micelles with the formula unit CDA$_4$-[DhS], wherein the DhS anions occupy a volume that is enclosed by CDA cations. The volume occupied by DhS anions may be dry (see Walters et al., *Inorg. Chem.* 44:1172 (2005) or may incorporate water in the manner of classical reverse micelles. The microemulsion serves as a precursor for the preparation of hyperbranched polymeric nanoparticles of DhS.

Embodiments of the present invention also relate to a contrast agent comprising the compound or molecular complex of formula (I) or (III), the hyperbranched polymeric nanoparticle or nanocapsule formed from the hyperbranched polymeric unit of formula (IV) and (V), or the mixed micelle described herein.

Accordingly, one aspect of the invention relates to a method of using the compound or molecular complex of formula (I)-(III), the hyperbranched polymeric nanoparticle or nanocapsule formed from formula (IV) and (V), or the mixed micelle described herein as a contrast agents. These contrast agents can be used in various areas, including but are not limited to, magnetic resonance imaging (MRI) analysis, nuclear magnetic resonance (NMR) analysis, florescence analysis, positron emission tomography (PET) analysis.

Lanthanoid ions can be selected for diamagnetism (La$^{3+}$) for NMR analyses, fluorescence properties (Eu$^{3+}$) or MRI contrast (Gd$^{34}$). Main group isotopes $^{68}$Ga$^{3+}$ or $^{111}$In$^{3+}$ can be incorporated in the monomers for PET.

In one embodiment, the molecular complex of formula (III), the hyperbranched polymeric nanoparticle or nanocapsule formed from formula (V), or the mixed micelle described herein can be used as a contrast agent in MRI analysis. An exemplary chelated metal used in these formulas is Gd.

In one embodiment, the molecular complex of formula (III), the hyperbranched polymeric nanoparticle or nanocapsule formed from formula (V), or the mixed micelle described herein can be used as a contrast agent in NMR analysis. An exemplary chelated metals used in these formulas is La.

In one embodiment, the molecular complex of formula (III), the hyperbranched polymeric nanoparticle or nanocapsule formed from formula (V), or the mixed micelle described herein can be used as a contrast agent in analyzing florescence properties. Exemplary chelated metals used in these formulas are Eu and Tb.

In one embodiment, the molecular complex of formula (III), the hyperbranched polymeric nanoparticle or nanocapsule formed from formula (V), or the mixed micelle described herein can be used as a contrast agent in PET analysis. Exemplary chelated metals used in these formulas are Ga and In, for instance, $^{68}$Ga and $^{111}$In.

An embodiment of the invention relates to a method of biomedical imaging. The method comprises administering to a patient the molecular complex of formula (III), the hyperbranched polymeric nanoparticle or nanocapsule formed from formula (V), or the mixed micelle described herein; and conducting a biomedical imaging test on the patient.

Another embodiment of the invention relates to a method of delivering a high concentration of contrast enhancing and/or imaging agents that comprises the step of administering to a patient the molecular complex of formula (III), the hyperbranched polymeric nanoparticle or nanocapsule formed from formula (V), or the mixed micelle described herein as a contrast agent. The chelated metal acts as the contrast enhancing and/or imaging agent.

Solid lipid nanoparticles (SLNs) offer an important route for the formation of multimodal theranostic agents, compared with noble metal particles. They are natural choices for the formation of theranostic agents because of their proven capacity to deliver drugs, and incorporate diagnostic molecules either on their surface or in their interior. The particle has been long valued for its utility in drug delivery particularly across the blood brain barrier (BBB). These particles are 50-200 nm in diameter and are composed of biocompatible lipids that are solid under ambient conditions. SLNs are inexpensive and often undergo disintegration in solution at rates that can be tailored to facilitate clearance.

Thus, embodiments of the invention relate to the hyperbranched shell encapsulating SLNs comprising the mixed micelle described above and a therapeutic agent. The therapeutic agent can be encapsulated within the mixed micelle. Additionally, the hyperbranched shell encapsulating SLNs described herein can be used as a drug delivery vehicle.

Accordingly, an embodiment of the invention also relates to a method of delivering drugs across physiological barriers, such as blood-brain barrier. The method comprises administering to a patient the hyperbranched shell encapsulating solid lipid nanoparticle described herein. The size of the hyperbranched shell encapsulating solid lipid nanoparticle for drug delivery typically ranges from 50-150 nm, or from 50-100 nm.

Any therapeutic agent known by those of skill in the art to have therapeutic activity can be contrained in the solid lipid nanoparticles. Suitable therapeutic agents include, but not limited to, chemicals, cells (including stem cells), proteins, peptides, nucleic acids (e.g., DNA, RNA, siRNA), nucleic acid analogues, nucleotides, oligonucleotides or sequences, peptide nucleic acids (PNA), aptamers, antibodies or fragments or portions thereof (e.g., paratopes or complementarity-determining regions), antigens or epitopes, hormones, hormone antagonists, cell attachment mediators (such as RGD), growth factors or recombinant growth factors and fragments and variants thereof, cytokines, enzymes, antioxidants, antibiotics or antimicrobial compounds, anti-inflammation agents, antifungals, viruses, antivirals, toxins, prodrugs, drugs, dyes, amino acids, vitamins, chemotherapeutic agents, and small molecules. The agent may also be a combination of any of the above-mentioned therapeutic agents.

In one embodiment, the therapeutic agent is a drug suitable for being delivered across physiological barriers, such as the blood-brain barrier.

In one embodiment, the therapeutic agent is an antibiotic or anti-tumor agent. Exemplary antibiotic agents include, but are not limited to, doxorubicin; actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxaciUin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents may also be antimicrobial peptides such as defensins, magainin and nisin; or lytic bacteriophage. The antibiotic agents can also be the combinations of any of the agents listed above.

In one embodiment, the therapeutic agent is doxorubicin. Doxorubicin is an anthracycline antibiotic and anti-tumor agent that intercalates DNA. It is effective against cancers that cause solid tumor formation as well as those that cause hematological malignancies (Booser & Hortobagyi, *Drugs* 47:223 (1994); Serpe et al., *Eur. J. Pharm. Biopharm.* 58:673 (2004), which are hereby incorporated by reference in their entirety). Its administration in solution as doxorubicin.HCl (DOX.HCl) causes many side effects, the most serious of which are cardiotoxicity, and myelosuppression (Subedi et al., *Eur. J. Pharm. Sci.* 37:508 (2009); Zara et al., *Pharmacol. Res.* 40:281 (1999), which are hereby incorporated by reference in their entirety). Improved safety can be achieved when doxorubicin is administered in lanthanoid-DOTA derivatives complex encapsulating SLNs. Free base DOX can be used for entrapment in the SLN core rather than its salts to avoid anions that could displace [LnDhS]⁻ during preparation of the core-capsule SLN.

The solid lipid nanoparticles are biodegradable and can dissolve into component small molecules that can be then cleared, likely through the kidneys. The lanthanoid-complex capsules are similarly biodegradable and can be cleared through the kidneys as molecular degradation products.

The hyperbranched shell encapsulating solid lipid nanoparticle described herein can be administered by various routes known to skilled in the art. One route is through intravenous administration. With normal kidney function, the gadolinium complexes should be eliminated from the circulatory system within 2-3 hours to avoid the accumulation of free $Gd^{3+}$ ions, which can cause nephrogenic systemic fibrosis (NSF) (Bongartz, *Magn. Reson. Mater. Phy.* 20:57 (2007); Penfield & Reilly, *Nat. Clin. Pract. Nephr.* 3:654 (2007), which are hereby incorporated by reference in their entirety). Following injection, the SLNs, which are relatively large, are confined to the circulatory system except where the leaky vasculature at solid tumor sites allows particles to extravasate, in some cases even as their diameters approach 600 nm (Yuan et al., *Cancer Res.* 55:3752 (1995), which is hereby incorporated by reference in its entirety). Particles that remain in circulation are taken up by the mononuclear phagocyte system (MPS) (Wisse et al., *Toxicol. Pathol.* 24:100 (1996), which is hereby incorporated by reference in its entirety). Rapid clearance of $Gd^{3+}$ complexes typically means that the GdDOTA capsule be readily hydrolyzed in the MPS. This cleavage can occur for ester links through acid hydrolysis in the endosome/lysosome compartments of leukocytes (Blasi et al., *Adv. Drug Deliver. Rev.* 59:454 (2007), which is hereby incorporated by reference in its entirety).

Intracellular biodegradation can occur either by disulfide bond reduction in the presence of glutathione in the cytosol or by ester hydrolysis in lysosome compartments of the cell (Lee et al., *Bioconjugate Chem.* 18:13 (2007); Roos et al., *Blood* 53:851 (1979), which are hereby incorporated by reference in their entirety). Hence cleavage of the capsule can occur followed by rapid clearance of the Ln-DOTA derivative complex via the kidneys and the liver (Wedeking & Tweedle, *Nucl. Med. Biol.* 15:395 (1988); Bui et al., *Pub. Lib. Sci. One* 5 (2010), which are hereby incorporated by reference in their entirety). Clearance of the solid lipid fraction would normally take place via the liver.

In one embodiment, to achieve biodegradability, the homoserine hydroxyl groups of Monomer 1 (LnDhS complex) are converted to ester acrylates (Monomer 2) (Scheme 3). The capsules are then assembled by photocrosslinking with appropriate initiator (Nguyen & West, *Biomaterials* 23:4307 (2002); Sawhney et al., *Macromolecules* 26:581 (1993), which are hereby incorporated by reference in their entirety).

Scheme 3

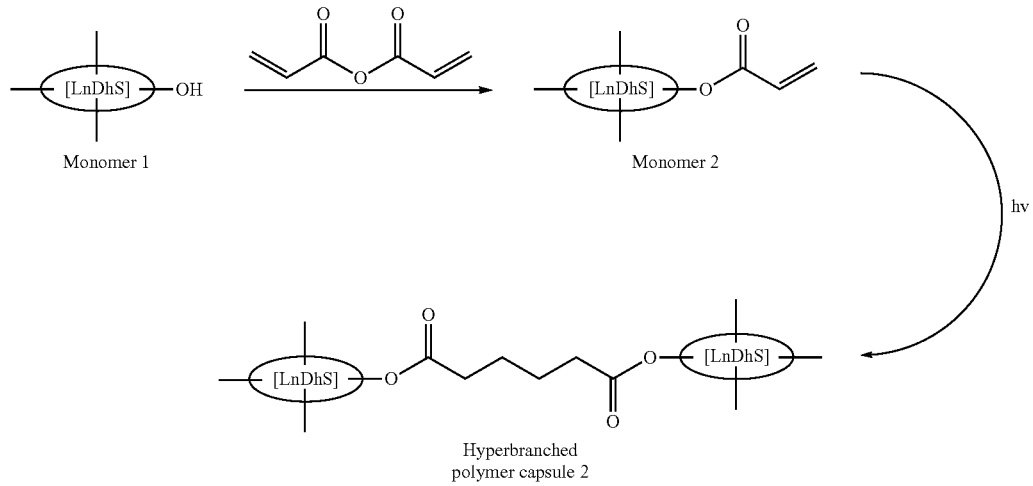

Monomer 1

Monomer 2

Hyperbranched polymer capsule 2

In one embodiment, to achieve biodegradability, acrylate group of Monomer 2 (LnDhS complex) is reacted with thiolacetic acid (Bullock et al., *J. Am. Chem. Soc.* 76:1828 (1954), which is hereby incorporated by reference in its entirety) followed by base hydrolysis to acquire the corresponding thiolates. The thiolates in the Stem layer of the mixed micelle (solid lipid nanoparticle) can be converted to a disulfide crosslinkers to assemble the capsule (Scheme 4).

Scheme 4

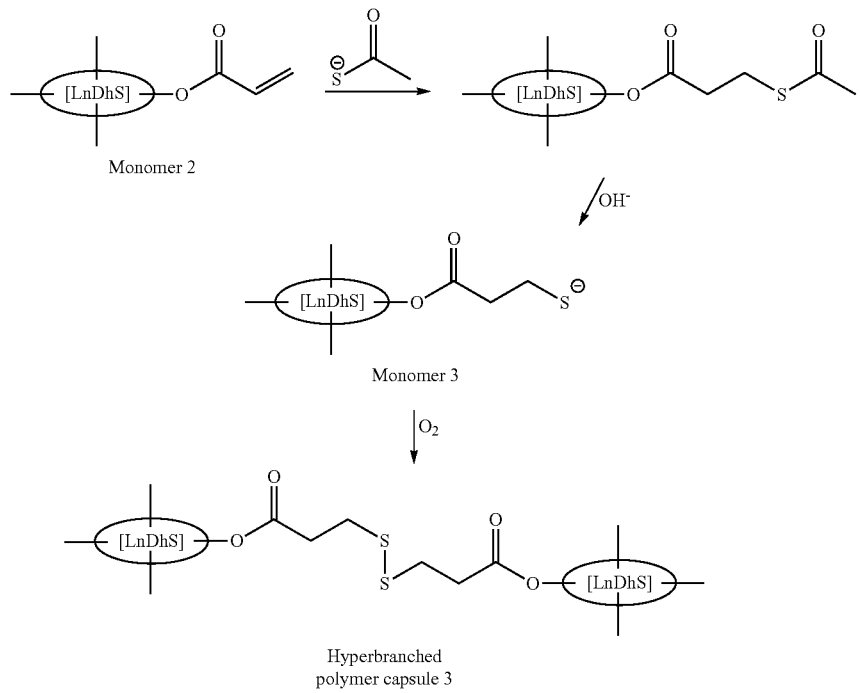

Hyperbranched polymer capsule 3

In one embodiment, to achieve biodegradability, the homoserine (LnDhS complex) is directly converted to homocysteine by halogenation (Br, or I) using standard methods followed by reaction with thioacetate, and acid hydrolysis. Oxidation of the thiol groups will then lead, as described above, to the formation of disulfide crosslinking groups to assemble the capsule.

Other aspect of the invention relates to a method of using the compound or molecular complex of formula (I) or (III), the hyperbranched polymeric nanoparticle or nanocapsule formed from formula (IV) and (V), or the mixed micelle described herein in catalysis reaction.

Yet another aspect of the invention relates to a method of using the compound or molecular complex of formula (I) or (III), the hyperbranched polymeric nanoparticle or nanocapsule formed from formula (IV) and (V), or the mixed micelle described herein in materials synthesis.

As used in this aspect of the invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "alkyl" refers to an aliphatic hydrocarbon group which may be linear, branched, or cyclic hydrocarbon structures and combinations thereof. Representative alkyl groups are those having 24 or fewer carbon atoms, for instance, methyl, ethyl, n-propyl, i-propyl, n-butyl, s-butyl, t-butyl, n-pentyl, i-pentyl, n-hexyl, and the like. Lower alkyl refers to alkyl groups having about 1 to about 6 carbon atoms in the chain. Branched alkyl means that one or more lower alkyl groups such as methyl, ethyl or propyl are attached to a linear alkyl chain.

The term "hydroxyalkyl" means an alkyl group is substituted with one or more hydroxy substituents, wherein the alkyl group is as herein described.

The term "mercaptoalkyl" or "thioalkyl" means an alkyl group is substituted with one or more mecaptan (thiol) substituents, wherein the alkyl group is as herein described. The term "radical of mercaptoalkyl" means a mercaptoalkyl where S atom carries a radical. For instance, radical of mercaptoethanyl refers to —$CH_2H_4$—S., wherein the —S. can readily bond to another radical to crosslink with a compound or molecular complex of formula (I), (II), or (III).

The term "alkylthioalkyl" means a thioalkyl group is substituted with one or more alkyl substituents, wherein the alkyl group is as herein described. Particularly, the thio group of the thioalkyl can be substituted with one or more alkyl substituents.

The above "alkyl", "hydroxyalkyl", "mercaptoalkyl", "radical of mercaptoalkyl", and "alkylthioalkyl" may be optionally substituted.

The term "arylalkyl" means an alkyl residue attached to an aryl ring. Examples are benzyl, phenethyl, and the like.

The term "substituted" or "optionally substituted" is used to indicate that a group may have a substituent at each substitutable atom of the group (including more than one substituent on a single atom), provided that the designated atom's normal valency is not exceeded and the identity of each substituent is independent of the others. In accordance with the present invention, up to three H atoms in each residue can be replaced with alkyl, halogen, haloalkyl, alkyenyl, haloalkenyl, cycloalkyl, cycloalkenyl, hydroxy, alkoxy, acyl, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, aryl, heteroaryl, aryloxy, or heteroaryloxy. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

In the characterization of some of the substituents, certain substituents may combine to form rings. Unless stated otherwise, it is intended that such rings may exhibit various degrees of unsaturation (from fully saturated to fully unsaturated), may include heteroatoms and may be substituted with other substituent groups as described above.

The term "cation" refers to an ionic species (i.e., an atom or a group of atoms) carrying a positive charge. Exemplary cations are $H^+$, $H_3O^+$, $Li^+$, $Na^+$, $K^+$, $Rb^+$, $Cs^+$, $Ag^+$, $Mg^{2+}$, $Ca^{2+}$, $Cu^{2+}$, $R_3NH^+$, $R_2NH_2^+$, $RNH_3^+$ (e.g., the protons of an alkylamine), etc.

The term "polymer precursor group" refers to a functional group for a compound or molecular complex (e.g., as shown in Formula (I) or (III)) that is able to self-crosslink or crosslink with the neighboring compound or molecular complex in presence of one or more crosslinking agent to form a polymer. For instance, —SH or —S. can be used as a polymer precursor for a compound or molecular complex to self-crosslinking through formation of disulfide bonds; —OH can be used as a polymer precursor for a compound or molecular complex in presence of appropriate crosslinking agent to form a polymer through formation of ether, ester, thioester, amide, disulfide bonds or combinations thereof.

The present invention may be further illustrated by reference to the following examples.

EXAMPLES

The following examples are intended to illustrate, but by no means are intended to limit, the scope of the present invention as set forth in the appended claims.

Example 1

Materials

Emulsifying wax was obtained from Spectrum Chemicals. Polysorbate surfactant (Brij® L23) and α-bromo-γ-butyrolactone were purchased from Sigma Aldrich Chemicals. Europium trichloride hexahydrate, gadolinium trichloride hexahydrate, divinyl sulfone (DVS) and potassium carbonate were purchased from Alfa Aesar Chemicals. Hexadecyl trimethyl ammonium chloride (CTA-Cl) was obtained from TCI America. All reagents were used as received.

Example 2

Preparation of Cyclen Tetrabytyrolactone

Cyclen (1.00 g, 5.80 mmol), potassium carbonate (4.00 g, 29.02 mmol) and α-bromo-γ-butyrolactone (6.03 g, 36.57 mmol) were refluxed for 3 days in $CH_3CN$. The filtrate was collected and the solvent was removed by rotary evaporation. A solid product was collected after several ether-wash/centrifugation cycles. The solid was redissolved in 15 ml chloroform, and extracted with 2×5 ml water. The chloroform solution was dried with magnesium sulfate and the solvent was removed by rotary evaporation to affort a yellow oil. Addition of diethyl ether produced the product as a yellow powder in 71% yield.

$^1$H NMR (400 MHz, $CDCl_3$, d): 4.45-4.25 (m, 8 H, O—$CH_2$), 3.95 (m, 4 H, N—CH), 3.70-3.49 (m, 4 H, cyclen-$CH_2$), 2.70-2.22 (m, 12 H, cyclen-$CH_2$), 2.40-2.25 (m, 8 H, lactone-$CH_2$); $^{13}$C NMR (400 MHz, $CDCl_3$, d): 178.5 (C=O), 65.18 (O—$CH_2$), 59.90 (N—CH), 47.22 (cyclen-$CH_2$), 21.25 (lactone-$CH_2$). ESI-MS m/z: 508.9 $[M+H]^+$, 531.9 $[M+Na]^+$, 546.9 $[M+K]^+$.

Example 3

Preparation of CTA-OH

CTA-Cl was stirred with KOH in anhydrous ethanol to prepare a stock solution of ethanolic cetyltritnethylammonium hydroxide (CTA-OH). The byproduct, KCl(s), was removed by filtration. The sample was stored as a 1 M stock solution in ethanol.

Example 4

Preparation of CTA[EuDOTA(N,N',N''',N'''''-tetra-a-homoserine)] (CTA[Eu(DhS)])

Cyclen tetrabutyrolactone (0.13 g, 0.26 mmol) and cetyltrimethylammonium hydroxide (CTA-OH) (1.6 mmol) were combined in 10 ml of ethanol and stirred overnight to open the butyrolactone rings by base hydrolysis. The ethanol was removed by rotary evaporation. The product was redissolved in 20 mL of methanol, and $EuCl_3.6H_2O$ was added in 1:1.1 ratio (0.105 mg, 0.29 mmol), under stirring for 3 hours. Methanol was removed by rotary evaporation. The remaining solid was redissolved in 25 mL of ethanol. After refluxing for 1 hour, 0.19 g CTA[Eu(DhS)], a 74% yield, was obtained as precipitate, leaving CTACl byproduct in the solution.

$^1$H NMR (400 MHz, $D_2O$, d): 41.9 (s, 4H, ring CH axial, minor isomer), 22.0 (s, 4H, ring CH axial, major isomer). 8.1 (s, 1H, ring CH axial major isomer), 4.1 (s, 4H, α-CH (homoserine sidechain)), 3.48 (m, 2H, α-N—$CH_2$ (CTA)), 3.0 (s, 9H, $CH_3$ (N—$CH_3$ from CTA), 1.6 (s, 2H, (3-N—$CH_2$ (CTA)), 1.2-1.0 (d, 26H, —$CH_2$— (CTA backbone)), 0.79 (m, 3H, —$CH_3$ (CTA terminal methyl group)), −0.5 (s, 8H, b-CH (homoserine sidechain)), −1.1 (s, 4H, γ-CH (homoserine sidechain)), −2.0 (s, 4H, γ-CH (homoserine sidechain)), −3.1 (s, 4H, ring CH equatorial, major isomer), −4.2 (s, 4 H, ring CH axial, major isomer), −4.9 (s, 4 H, ring CH equatorial, minor isomer), −8.6 (s, 4 H, ring CH equatorial, major isomer), −12.1 (s, 4 H, CH), −25.4 (s, 4 H, CH-minor isomer). ESI-MS m/z: 729.0 $[M]^-$.

Example 5

Preparation of CTA[GdDOTA(N,N',N''',N''''-tetra-a-homoserine)] (CTA[Gd(DhS)])

The product CTA[Gd(DhS)] was obtained from $GdCl_3 \cdot 6H_2O$ (0.29 mmol) by the method described above in Examples 2-4 in the synthesis of the europium complex. ESI-MS m/z: 734.3 [M]$^-$.

Example 6

Formation of [EuDhS]SLN using Brij® L23

The solid lipid nanoparticles were prepared in a microemulsion following the method of Oyewumi and Mumper (Oyewumi & Mumper, *Drug Dev. Ind. Pharm.* 28:317 (2002), which is hereby incorporated by reference in its entirety). Solutions of (i) emulsifying wax in chloroform and (ii) other reagents in water were freshly prepared before the synthesis. Emulsifying wax, 4 mg in 60 μl of chloroform from a stock solution, was deposited in a glass vial by evaporating the chloroform solvent. The solidified wax in the glass vial was heated to 55° C., and 1 ml distilled water was added dropwise while stirring at 1500 rpm and maintaining the temperature at 55° C. A homogenous milky slurry was formed, at which point 60 μL of 100 mM Brij® L23 ($C_{12}H_{25}(OC_2H_4)_{23}OH$) solution (6 μmol) was added. After 2 minutes, 1200 μL of 50 mM CTA$^+$[Eu(DOTA)(N,N',N''',N''''-tetra-a-homoserine)]$^-$ solution (60 μmol) was added. The solution was stirred until it became transparent (about 30 minutes) and then was cooled on an ice bath to form SLNs. The SLN colloidal solution was then diluted with the addition of 1 ml cold water at 4° C. and filtered through a 0.22μ pore size membrane to remove large particles. The obtained SLN solution was stored at 4° C. for further use.

Example 7

Formation of [EuDhS]$_{CL}$SLN

Crosslinking of the surface hydroxyls of [EuDhS]$^-$ was carried out by adding divinylsulfone (DVS) to the solution of [EuDhS]SLN, such that DVS and CTA[Eu(DhS)] surfactant are in 1:4.17 molar ratio. The pH of the [EuDhS]SLN solution was raised to a value of 12.0 by adding 1.0 M NaOH solution dropwise. After the desired pH was reached, 25 μL DVS solution (0.25 mmol) was added very slowly over a period of 5-10 minutes. The resulting solution was allowed to react for 3-6 hours. After that, the pH was lowered to 7.5-8 by the slow addition of 1.0 M HCl (aq.). Samples were stored as aqueous colloidal solutions at 4° C. The samples remained transparent for at least 8 weeks.

Example 8

Characterization

Proton NMR data were obtained on a Bruker Avance 400 MHz NMR spectrometer. Relaxivity measurements were carried out in deionized water ($H_2O$) solutions at 25° C. with the temperature controlled by a BVT-3200. The aqueous ($H_2O$) samples were contained in the internal capillary tubes of a coaxial cell with the $D_2O$ lock solvent in the exterior (5 mm o.d.) chamber. Acquisition parameters were: time domain 16K complex data point; 6410.26 Hz sweep width; 90° pulse with a length of 9 μs, at a power level of 5.00 dB repetition time $T_R$ of 45 s; variable inversion time delay (τ) ranging from 100 ms to 5 s. Spectra were processed with XWIN-NMR version 3.5.6 to obtain relaxation curves.

Electrospray ionization (ESI) mass spectrometric data were obtained using an Agilent 1100 Series Capillary LCMSD Trap XCT MS spectrometer.

Inductively coupled plasma optical emission spectroscopy (ICP-OES) chemical analyses were carried out by Galbraith Laboratories.

TEM images were acquired on a Philips CM-12 electron microscope. Samples were prepared on carbon coated copper grids and the micrographs were recorded on a Gatan 1k×1k digital camera.

Fluorescence data was collected on a Hitachi F-2500 fluorescence spectrophotometer.

Dynamic light scattering measurements were carried out on a Brookhaven Instruments ZetaPALS/Zeta Potential Analyzer and a Beckman-Coulter N4 Plus instrument.

Example 9

Ligand Synthesis and Particle Formation

Cationic SLNs have been employed primarily as vehicles for DNA and RNA transfer (Kim et al., *Mol. Pharm.* 5:622 (2008); Tabatt et al., *Eur. J. Pharm. Biopharm.* 57:155 (2004); Siddiqui et al., *Int. J. Pharm.* 400:251 (2010), which are hereby incorporated by reference in their entirety). In that capacity they provide matrices for the adsorption and delivery of nucleic acid oligomers via endocytosis of the SLN. The desirable cationic surfactants for the fabrication of gene transfer SLNs are biodegradable and non-cytotoxic as a result of their twin-tailed lipid structure (Tabatt et al., *Eur. J. Pharm. Biopharm.* 57:155 (2004), which is hereby incorporated by reference in its entirety). These surfactants are paired with simple halide counterions that are later replaced by polyanionic DNA. Satisfactory cationic SLNs for in vitro studies are also available with simple single-tailed cationic surfactants such as cetyltrimethylammonium bromide (CTAB). The halides are later replaced by polyanionic DNA. CTA$^+$ was used in Examples 1-8, but with a unique approach that substituted functional anions for simple halides such as Br$^-$. The functional anions then provided precursor monomers for polyanionic shell formation.

The work in Examples 1-8 focuses on the incorporation of EuDOTA in SLN-based particles. Early fluorescence measurements suggested that the uptake of anionic hydrophilic LnDOTA complexes into a hydrophobic SLN core was unfavorable. The work described herein, however, demonstrates an unprecedented method, by which the LnDOTA complex nanocapsules synthesized were assembled on a charged colloidal surface and then crosslinked to form a hyperbranched enclosure around the SLN. Briefly, cationic surfactants were employed to stabilize the SLN surface (Eccleston, *Colloid. Surface. A* 123:169 (1997); Kim et al., *Mol. Pharm.* 5:622 (2008); Tabatt et al., *Eur. J. Pharm. Biopharm.* 57:155 (2004); Siddiqui et al., *Int. J. Pharm.* 400:251 (2010), which are hereby incorporated by reference in their entirety). The counterions consisted of the monoanionic complex [EuDOTA(homoserine)4⁻ ([EuDhS]⁻), in which four hydroxyethyl groups are attached to the α carbons of DOTA. A micelle coronal crosslinking method was employed to form the capsule (Liu et al., *Langmuir* 18:7780 (2002); Read & Armes, *Chem. Comm.* 3021 (2007), which are hereby incorporated by reference in their entirety).

This system is unique in its incorporation of [Eu(DOTA-N,N',N'',N'''-tetrahomoserine)]-([EuDhS]⁻) as a monoanionic counterion to CTA⁺ (Scheme 5).

Scheme 5. CTA⁺[Eu(DOTA-N, N', N'', N'''-tetrahomoserine)], CTA [EuDhS].

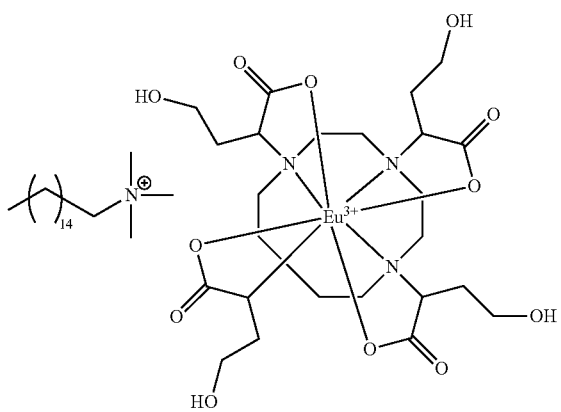

It differs from preceding work in that it entails the assembly of complex counterions in a polymeric network on a solid lipid nanoparticle (SLN) surface (Gao et al., *J. Colloid Interf. Sci.*, 273:626 (2004), which is hereby incorporated by reference in its entirety). This system appears to be the first capsule formed by crosslinking the lanthanide DOTA complexes; this system also appears to be the first capsule formation around a solid lipid nanoparticle to generate a multimodal/multifunctional particle by virtue of the presence of functional groups in the capsule layer.

[EuDhS]⁻, the complex serving as the functional anion, was prepared by reacting R,S-bromobutyro lactone with cyclen to form DOTA-N,N',N'',N'''-tetrabutyrolactone, similar to the method described in Lazlo et al. (Lazar et al., *Eur. J Org. Chem.* 351 (2002), which is hereby incorporated by reference in its entirety). Lactone ring-opening by base hydrolysis with CTA(OH) gave a cyclic octadentate DOTA-tetrahomoserine derivative. The europium compound $EuCl_3$ was then added to form the complex [EuDhS]⁻ in which europium was coordinated by the four amine groups and four carboxylate groups to form an eight-coordinate EuDOTA complex (Scheme 2). In the formation and workup of the complex, three equivalents of the CTACl byproduct were removed, leaving one equivalent of CTA to form the isolable salt CTA⁺[EuDhS]⁻. The four pendant hydroxyethyl groups of the ligand were utilized to form a hyperbranched poly EuDOTA capsule.

The solid lipid nanoparticle core was prepared from emulsifying wax and Brij® L23, using a method similar as described in Oyewumi and Mumper (Oyewumi & Mumper, *Drug Dev. Ind. Pharm.* 28:317 (2002), which is hereby incorporated by reference in its entirety). Emulsifying wax (EW) is a multicomponent matrix that consists of cetylstearyl alcohol and polysorbate 60 (USP28-NF23, 2005 Edition of the United States Pharmacopeia and National Formulary (USP-NF), page 3107). The wax resists crystallization and therefore provides an amorphous matrix that favors the inclusion of additives (Ulrich, *Biosci. Rep.* 22:129 (2002), which is hereby incorporated by reference in its entirety). EW nanoparticles were formed in an oil/water (o/w) microemulsion at 55° C. The o/w emulsion was stabilized by the addition of the surfactants Brij® L23 and cetyltrimethylammonium (CTA⁺). Subsequent rapid cooling from 55° C. to 4° C. solidified the molten wax to yield cationic SLNs. Examples 1-8 use CTA⁺[EuDhS]⁻/Brij® L23 mixed surfactant system for the SLN. Although CTA⁺Br⁻/Brij 35 mixed micelles were described in Gao et al. (Gao et al., *J. Colloid Interf. Sci.*, 273:626 (2004), which is hereby incorporated by reference in its entirety), the surfactant system prepared in Examples 1-8 uses a unique approach that employs a functional anion instead of simple halides. This functional anion, [EuDhS]⁻, provided precursor monomers for polyanionic shell formation.

Figure 4:
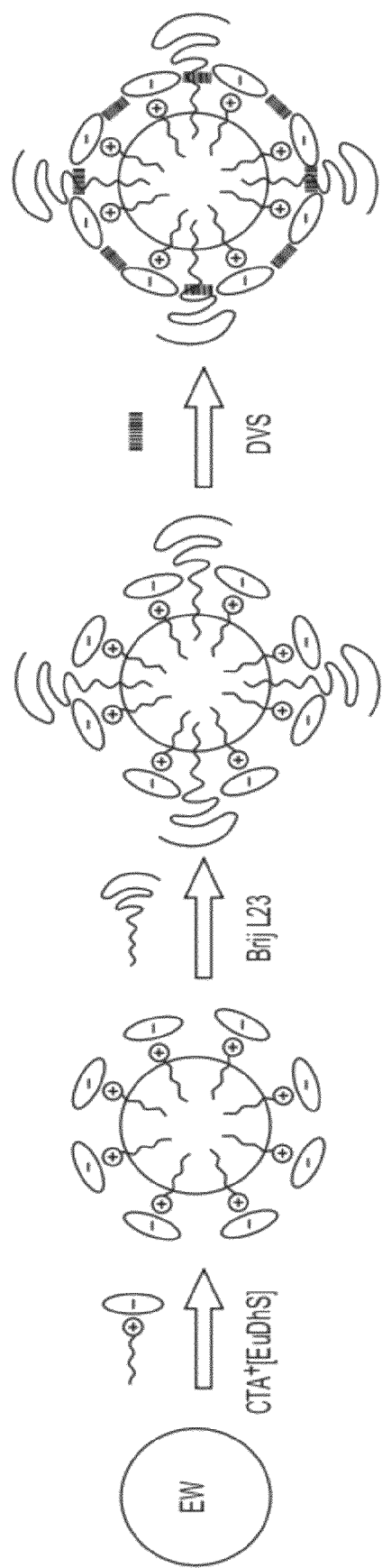
FIG. 4 is a schematic illustration of the process of CTA[EuDhS]$_{CL}$SLN synthesis where CL refers to a crosslinking moiety and EW denotes the emulsifying wax core.

After the forming of the SLN colloidal solution of CTA⁺[EuDhS]⁻/Brij® L23, the crosslinking agent divinyl sulfone (DVS) was added to the SLN colloidal solution to generate a hyperbranched polymer shell from the monoanionic europium complexes [EuDhS]⁻. The shell enclosed the cationic SLN to form an electrostatically associated core-shell assembly. See FIG. 4.

Several literatures have described MRI contrast-enhancing SLNs. These include the work of Morel et al. that reported the incorporation of GdDTPA and GdDOTA in SLNs as MRI contrast agents (Morel et al., *Eur. J. Pharm. Biopharm.* 45:157 (1998), which is hereby incorporated by reference in its entirety). Report by Zhu et al. provided a detailed analysis of an emulsifying wax SLN bearing a surfactant with a GdDTPA headgroup (Zhu et al., *J. Nanosci. Nanotechnol.* 6:996 (2006); Sun et al., *Magn. Reson. Med.* 65:673 (2011), which are hereby incorporated by reference in their entirety). Another report described a similar study with the improvement that the SLN is cationic that associated with the dianionic contrast agent $[GdDTPA]^{2-}$ (Chen & Zhang, *Chinese J. New Drugs* 18:1443 (2009), which is hereby incorporated by reference in its entirety). For all these above systems described in the literature, the locations and related relaxivity of Gd complexes have not been discussed.

In contrast, the spatial distribution of fluorescent lanthanide DOTA complex relative to the SLN core has been described herein. The association of (CTA)[EuDhS] with an emulsifying wax SLN formed from molten microemulsion is expected to yield a stable composition in electrolyte-free aqueous solution. The Stern layer of the particle would consist of surface CTA ammonium headgroups interspersed with the anionic europium complexes (Schemes 5 and 6).

Scheme 6. Divinyl sulfone crosslinking of [EuDhS]⁻ counterions that form a Stern layer with cations on the SLN surface
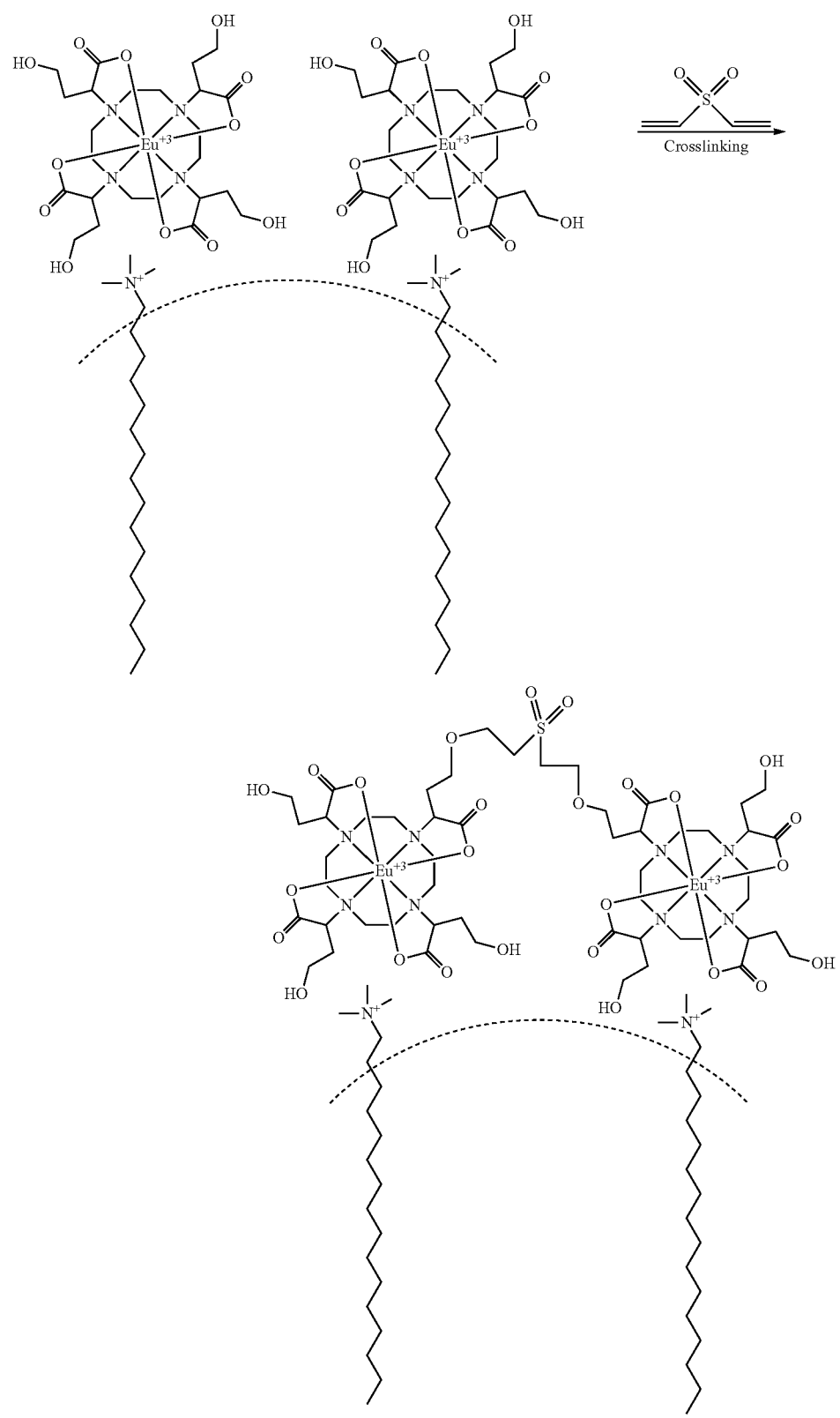

In forming a polymerized capsule of [EuDhS]⁻ around an SLN core, Brij® L23 and CTA[EuDhS] were combined with molten emulsifying wax in an oil-in-water (o/w) microemulsion. Upon solidification, the resulting nanoparticles consisted of a core of emulsifying wax in which the lipophilic tails of CTA (—$C_{16}H_{33}$) were anchored and interspersed with the lipophilic tails of Brij® L23 (—$C_{12}H_{25}$). The anionic counterion was crosslinked to form mixed micelles that combined charged surfactants and counterions with neutral, unreactive and bulky diblock copolymer surfactants such as Brij® L23. This SLN system was selected for biomedical applications because of its core stability, functionality, and size selection provided by SLNs.

Charged surfactants can either form a micelle or stabilize the surface of an SLN core by using surfactants. However, the stable, functional SLN system described herein cannot be readily achievable by micelles formed through simpling mixing surfactants. Without crosslinking the anions, the [EuDhS]⁻ anions were expected to form mobile species in the Stern layer with the CTA headgroup cations. The route to [EuDhS]⁻ incorporation in an SLN-enclosing capsule includes a precursor in which the complex is partitioned between the Stern layer and the double layer in the vicinity of the SLN core. In this spatial arrangement, the anions within the Stern layer are, by design, sterically isolated by the Brij® L23 polyether-$(C_2H_4O)_{23}$—OH chains. In aqueous solution at high ionic strength, anion exchange is expected to displace much of the complex from the particle surface. The assembly is also unstable in simple aqueous media on a longer time scale because of the disintegration or aggregation of the SLN cores (Oyewumi & Mumper, *Drug Dev. Ind. Pharm.* 28:317 (2002), which is hereby incorporated by reference in its entirety). As a remedy, the SLN assembly can be stabilized against both anion diffusion and core disintegration or aggregation by crosslinking the anionic complexes. This process can be described as emulsion surface polymerization (ESP).

The crosslinking reaction was carried out in aqueous solution by the reaction of divinyl sulfone (DVS) with the pendant hydroxyethyl groups of the anionic [EuDhS]⁻ complexes. Through this approach a capsule was formed by a hyperbranched polymer network enclosing a cationic SLN, [EuDhS]$_{CL}$SLN (Scheme 6). Although a crosslinking reaction in block copolymer micelles has been reported (Liu et al., *Langmuir* 18:7780 (2002); Read & Armes, *Chem. Comm.* 3021 (2007), which are hereby incorporated by reference in their entirety), such reactions have not been used to crosslink SLN to stabilize the SLN assembly.

In the solid EW particle the lipophilic tails of CTA⁺ (—$C_{16}H_{33}$) and Brij L23 (—$C_{12}H_{25}$) are embedded in the lipid, leaving the cationic headgroup of CTA⁺ and the polyoxomer block of Brij L23 exposed to the aqueous bulk phase. The [EuDhS]⁻ counteranion monomers are expected to occupy the Stern layer as mobile species that exchange among fixed-position cationic CTA headgroups of the particle (CTA [EuDhS]SLN). The anionic complexes, [EuDhS]⁻ are subject to mass action involving small ions, such as Cl⁻ in high salt solutions, that can displace [EuDhS]⁻ complexes from the SLN surface. As with SLNs in general, the NP, CTA[EuDhS] SLN, is unstable in simple aqueous media on longer time scales because of the well known tendency for disintegration or aggregation. Crosslinking to form the hybrid particle (CTA)[EuDhS]$_{CL}$SLN prevented anion displacement, and stabilized the particles against core disintegration and aggregation.

The crosslinking step was carried out at room temperature after formation of solid lipid nanoparticles. Crosslinking produces a hyperbranched polymer network that encloses the cationic SLN to form the hybrid NP [EuDhS]$_{CL}$SLN (Scheme 6). The anionic complex monomers within the Stern layers of adjacent particles are sterically separated by the polyether —$(C_2H_4O)_{23}$—OH chains of Brij L23, which prevents interparticle crosslinking.

Example 10

Europium Fluorescence

Figure 5:
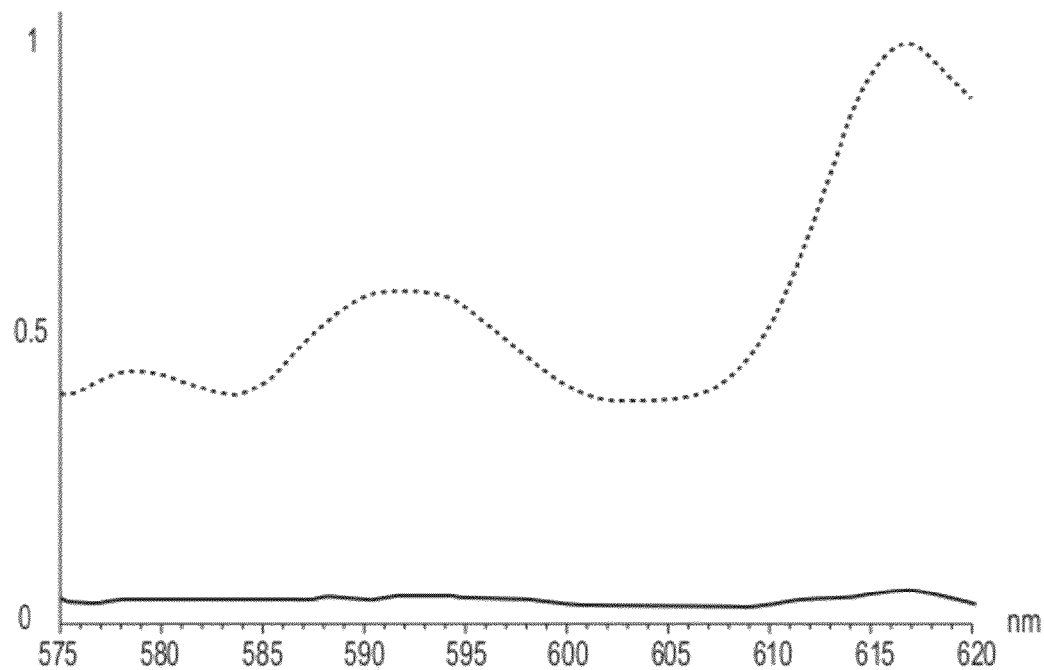
FIG. 5 is a graph showing the fluorescence spectra of NaCl(aq)-treated [EuDhS]SLN (red), and the salt-free control [EuDhS]SLN (green).

In order to validate the requirement for crosslinking to stabilize the assembly, fluorescence was used to monitor the displacement of europium complexes from the SLN surface in an aqueous salt solution, comparing the SLN system with and without crosslinking. Excitation of the [EuDhS]⁻ complex at 319 nm generated emission peaks at 578, 592 and 617 nm. The fluorescent emission of the core solid lipid at 406 nm did not interfere with measurements in the region of the europium emission. The [EuDhS]SLN sample was dialyzed against approximately 50 ml 0.68 M sodium chloride, a 2000 fold excess of Na⁺, and compared to a salt-free [EuDhS]SLN control that was dialyzed against distilled water, using a 2.0 kDa cutoff dialysis membrane. After 24 hours of dialysis, the europium emission peak at 617 nm decreased by 94%; the fluorescence of the control was unchanged (FIG. 5). The loss of fluorescence intensity indicates the displacement of [EuDhS]⁻ complex from the [EuDhS]SLN surface by aqueous Cl⁻, when there is no crosslinking.

Figure 6:
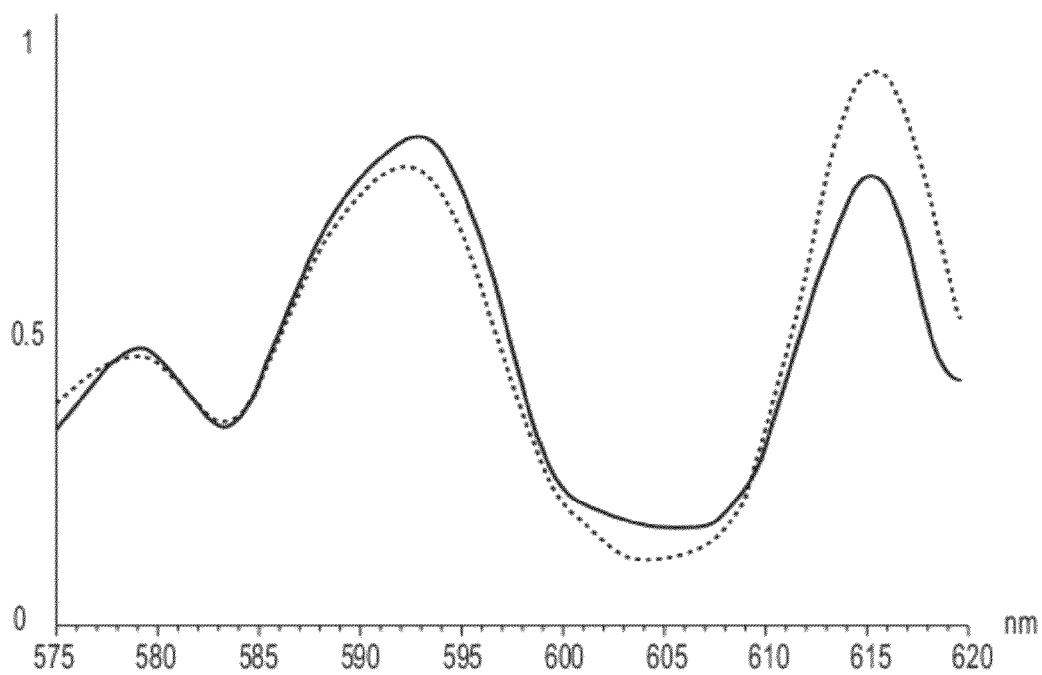
FIG. 6 is a graph showing the fluorescence spectra of NaCl(aq)-treated [EuDhS]$_{CL}$SLN (red) and the salt-free control [EuDhS]$_{CL}$SLN (green).
Figure 7:
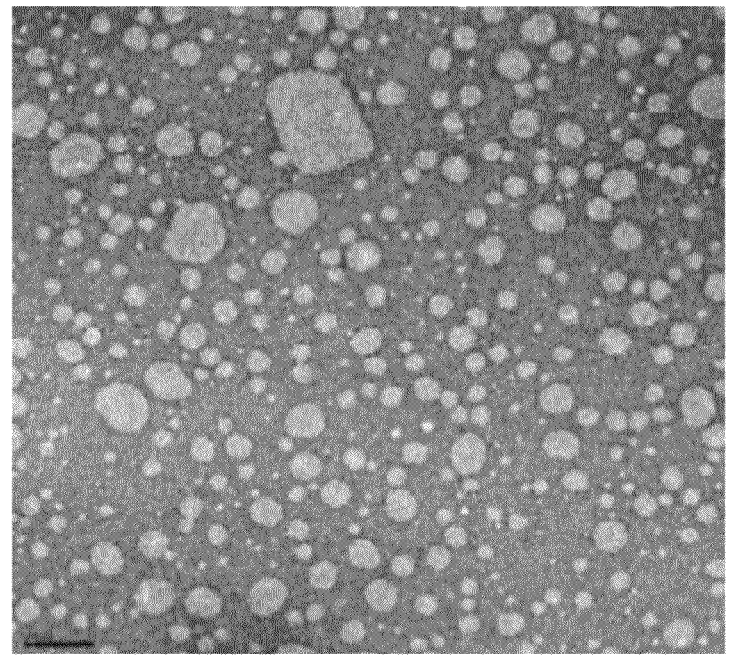
FIG. 7 is a graph showing TEM image of SLN particles. (Bar represents 100 nm).

Emulsion surface polymerization (ESP) was conducted to the SLN system by adding divinyl sulfone (DVS) to a solution of [EuDhS]SLN. The cross-linking step was allowed to proceed at room temperature for a period of 3-6 hours. The crosslinked product, [EuDhS]$_{CL}$SLN, was purified by dialysis against distilled water, and stored as an aqueous solution under refrigeration. It was then tested for stability by dialysis against aqueous NaCl using the procedures as described above. As shown in FIG. 6, in the crosslinked sample, [EuDhS]$_{CL}$SLN, only 19% of the [EuDhS]⁻ complexes were displaced by Cl⁻ (FIG. 6). These results show that the Eu complexes reside only within the Stern and double layer regions at the SLN surface. The results prove the efficacy of [EuDhS]⁻ crosslinking in forming a stable capsule that encloses the cationic SLN core. Further, based on transmission electron microscopic (TEM) data (FIG. 7), crosslinking between adjacent SLN particles is absent, likely the outcome of Brij® L23 steric barriers.

Further, the concentration of Eu complexes in the solid lipid core must be negligible because Eu fluorescence is absent after the displacement of [EuDhS]⁻ by Cl⁻ ions. Support for this conclusion is provided by a report that europium complexes exhibit fluorescence of comparable intensity both in solution and in sol-gel derived materials (Matthews et al., *Chem. Mater.* 5(12): 1697-1700 (1993), which is hereby incorporated by reference in its entirety.). Therefore it was believed that significant amounts of [EuDhS]⁻ within the SLN matrix would be observable by fluorescence. This fluorescence would persist even after the displacement by Cl⁻ of [EuDhS]⁻ complexes in the Stern layer external to the SLN core.

Example 11

Solid Lipid Nanoparticle Characteristics

An average hydrodynamic diameter of 51.0±10.9 nm (polydispersity index of 0.6) was found for [EuDhS]$_{CL}$SLN by dynamic light scattering (DLS) measurements. A zeta potential of +10.7 mV was measured by Doppler shift light scattering at pH 7.0. TEM images show that particles are polydisperse, but most abundant in the 50 nm range and with nearly spherical geometry.

The number of SLN particles per sample was determined from the total mass of emulsifying wax in the sample, the density of the wax, 0.85 g/cm$^3$, and the average particle size as determined by DLS and TEM data. The result shows there are $1.64 \times 10^{13}$ particles per mL aqueous solution. The concentration of [EuDhS]$^-$ was determined from magnetic susceptibility measurements to be 0.73 mM $2.64 \times 10^{17}$ ions in a sample containing $1.64 \times 10^{13}$ particles, where the effective magnetic moment of Eu$^{3+}$ is 3.40 at 25° C. (Peters et al., *Prog. Nucl. Magn. Reson. Spectrosc.* 28:283 (1996), which is hereby incorporated by reference in its entirety). The average number of [EuDhS]$^-$ ions per [EuDhS]$_{CL}$SLN shell is therefore $8 \times 10^3$ ions for a 65 nm diameter particle. This is smaller than the $34 \times 10^3$ ions expected (Siddiqui et al., *J. Colloid Interf. Sci.* 337:88 (2009); Zhu et al., *J. Nanosci. Nanotechnol.* 6:996 (2006), which are hereby incorporated by reference in their entirety). Perhaps the degree of hyperbranched crosslinking of the SLN assembly is less than ideal due to a combination of factors of steric barriers, DVS hydrolysis or suboptimal reactant ratios.

Additional dynamic light scattering measurements also gave an average hydrodynamic diameter of 65.1±7.3 nm for [EuDhS]$_{CL}$SLN. The zeta potential of the crosslinked particle was +10.7 mV as measured by Doppler shift light scattering at pH 7.0. The particles were polydisperse by transmission electron microscopy, but were most abundant in the 50 nm range and with nearly spherical geometry. Smaller spherical particles were observed with diameters in the 5-10 nm range while larger particles appeared to be aggregates with diameters in the range of 100 nm. See FIG. 7.

From ICP-OES analysis of 5 mg of [EuDhS]$_{CL}$SLN, europium was found at the level of 187 ppm (1.23 µmol) which corresponds to $7.41 \times 10^{17}$ Eu ions in the sample. Assuming a uniform particle density of 0.85 g/cm$^3$, and an average diameter of 65.1 nm, the 5 mg sample contains $4.07 \times 10^{13}$ SLN particles with an average of $1.8 \times 10^4$ Eu complexes per particle.

Example 12

NMR Analysis

Figure 8:
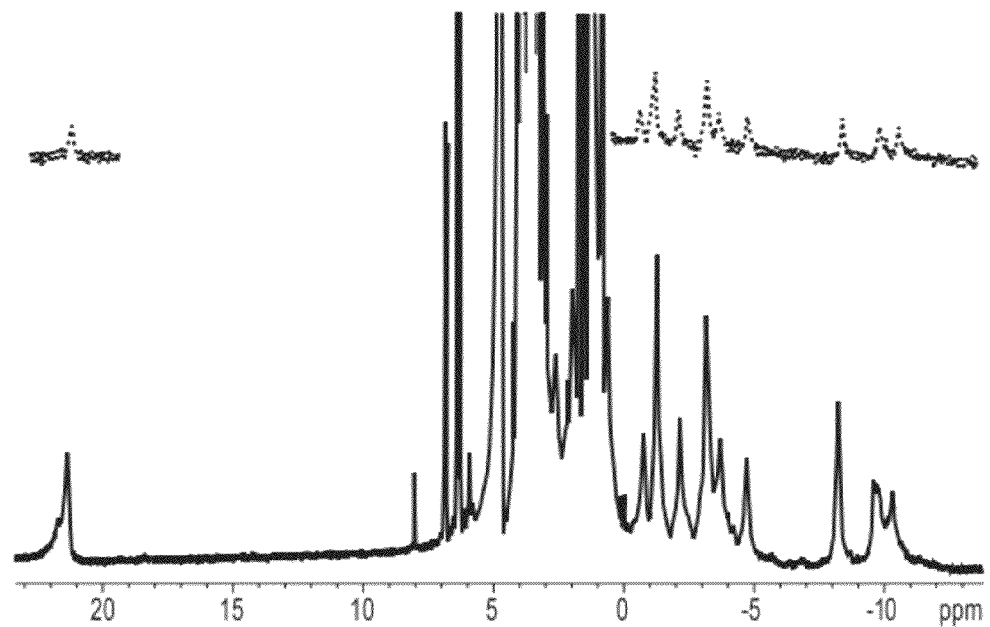
FIG. 8 is a graph showing the proton NMR spectrum of CTA[EuDhS]$_{CL}$SLN in D$_2$O. The insets show the proton NMR spectrum of K[EuDhS] in D$_2$O.

Europium (III) is paramagnetic due to low-lying states with J>0, just above the diamagnetic $^7F_0$ ground state. In [EuDhS]$^-$, the Eu$^{3+}$ ion serves as a shift reagent, which complements its fluorescent properties. Free complexes exhibit a room temperature $^1$NMR spectrum that is broadly congruent with that reported earlier for [EuDOTA]$^-$ (Aime et al., *Inorg. Chem.* 36:2059 (1997); Desreux, *Inorg. Chem.* 19:1319 (1980); Aime et al., *Inorg. Chem.* 31:4291 (1992); Woods et al., *J. Am. Chem. Soc.* 122:9781 (2000), which are hereby incorporated by reference in their entirety). The expected dipolar shifts of cyclen protons induced by europium appeared as a range of peaks in the upfield 0-(−11) ppm region, and a peak with a shoulder 21 ppm downfield with a peak from the adventitious proton peak at 4.7 ppm in D$_2$O solvent (FIG. 8). As shown in FIG. 8, the peaks of the shell-localized complexes of [EuDhS]$_{CL}$SLN with large upfield and downfield displacements were congruent with the corresponding peaks of the free complex [EuDhS]$^-$ (inset); peaks in the 0-7 ppm downfield region are assigned to homoserine sidechain, crosslinkers and SLN core protons, as would be expected with the distance attenuation of dipolar shifts. Peak assignments cannot be obtained from room temperature spectra of racemic EuDOTA derivatives because of structural isomerization, in which case peaks from the diasteriomers δδδδ, δλλλ, δδλλ and δλδλ overlap (Woods et al., *J. Am. Chem. Soc.* 122:9781 (2000), which is hereby incorporated by reference in its entirety).

Example 13

Gadolinium Relaxivity

Liposomal MRI contrast agents have been described to incorporate Gd complexes at both the inner and outer lipid/water interfaces. As expected, the relaxivity for the inner interface diminishes by the decreased rate of water exchange between the inner and outer aqueous regions (Muller et al., *Langmuir* 24:4347 (2008), which is hereby incorporated by reference in its entirety). An earlier study described gadolinium complexes in SLNs (Morel et al., *Eur. J Pharm. Biopharm.* 45:157 (1998), which is hereby incorporated by reference in its entirety). However, whether it can be used as contrast agent and the mechanism of contrast enhancement are unknown, because the locations of the polar Gd contrast agents were unknown in that study. Zhu et al. employed a lipid tethered GdDTPA complex that was incorporated in the surfactant layer of an SLN (Zhu et al., *J. Nanosci. Nanotechnol.* 6:996 (2006), which is hereby incorporated by reference in its entirety). However, the convenience and efficacy of this approach may be greatly offset by the expense of lipid precursors. It is therefore desirable to attach Gd complexes by simple, but easily accessible linkages.

As shown by Morel et al., gadolinium complexes associated with solid lipid nanoparticles generally display T$_1$ relaxivities comparable to simple molecular agents in aqueous solution (Morel et al., *Eur. I Pharm. Biopharm.* 45:157 (1998), which is hereby incorporated by reference in its entirety). This result suggests that active Gd complexes reside at the lipid/water interface. Interior Gd complexes will not likely be accessible for water exchange, and thus will not induce inner sphere relaxation of water proton spins. Morel et al. offered two alternative explanations for the mono-exponential free induction decay of the water proton magnetization in their Gd/SLN system. One suggestion was that the Gd complexes were embedded in the lipid core with fast exchange of water molecules occurring between the compartments. A second hypothesis was that no exchange takes place between the compartments; rather, only Gd complexes on the outer surface contributed to water relaxation. Both explanations reasonably imply that Gd$^{3+}$ ions must be in proximity to bulk water to induce significant proton relaxation. To optimize relaxivity for liposomal delivery vehicles, Gd complexes typically need to be attached to the outer layer of the liposomal bilayer liposomal delivery vehicles (Kamaly & Miller, *Int. J. Mol. Sci.* 11:1759 (2010), which is hereby incorporated by reference in its entirety).

The congeners [GdDhS]$^-$ and [GdDhS]$_{CL}$SLN were prepared from the product of GdCl$_3$.6H$_2$O and DhS$^{4-}$. The r$_1$ relaxivities of the Gd[DhS]$^-$ and Gd[DhS]$_{CL}$SLN were found to be 4.16 and 7.70 s$^{-1}$ mM$^{-1}$, respectively, at 9.4 T (400 MHz) NMR and 25° C. (Table 1). The corresponding whole particle relaxivity of Gd[DhS]$_{CL}$SLN is r$_1$=2.09×10$^5$ mM$^{-1}$.

TABLE 1

Relaxivity ($r_I$) per Gd, or per particle in $H_2O$ at 9.4 T (400 MHz), 25° C.

| Compound | Complexes per particle | Relaxivity ($s^{-1}mM^{-1}$) |
|---|---|---|
| Gd[DTPA]$^{2-}$ | | 4.6[a] |
| Gd[DhS]$^-$ | | 4.16 |
| Gd[DhS]$_{CL}$SLN | | 7.70 |
| Gd[DhS]$_{CL}$SLN | 18000 | 209000[b] (per particle) |

[a]Siddiqui et al., *J. Colloid Interface Sci.*, 337(1): 88-96 (2009).
[b]Relaxivity per particle is estimated from the Gd$^{3+}$ population on the particle surface.

Several reports have described the use of SLNs for MRI contrast enhancement (Morel et al., *Eur. J. Pharm. Biopharm.* 45:157 (1998); Zhu et al, *J. Nanosci. Nanotechnol.* 6(4):996-1003 (2006); Sun et al., *Magn. Reson. Med.* 65(3):673-79 (2011); Chen et al., *Zhongguo Xinyao Zazhi* 18(15):1443-47 (2009), all of which are hereby incorporated by reference in their entirety). In general for these systems the locations and/or relaxivities of the Gd complexes were not directly discussed. By contrast, the work described here focused on the spatial distribution of [EuDhS]$^-$ complex relative to the SLN core, by measuring the related relaxivity of the congener [GdDhS]$^-$ complex of the [LnDhS]$_{CL}$SLN system.

In the early work by Morel et al., gadolinium complexes associated with solid lipid NPs had $r_1$ relaxivities comparable to simple molecular agents. Results from more recent studies suggest that $r_1$ relaxivity values ≥4-5 s$^{-1}$ mM$^{-1}$ derive only from surface localized Gd complexes.

In the system described in Examples 1-13, a method has been described that can significantly expand the role of SLNs by making them multimodal using a simple and cost effective synthetic tools. In this method, cationic solid lipid nanoparticles have been prepared herein with europium DOTA complexes as counterions. The europium DOTA complexes have pendant hydroxyl groups that act as precursors for Stern layer polymerization using DVS crosslinking. The process is referred to as emulsion surface polymerization (ESP). Further, from the fluorescence results, the locations of fluorescent lanthanoid complexes relative to SLN have been readily ascertained. Additionally, this system provides a convenient route to assemble a contrast agent with LnDOTA restricted to the surface with the core reserved as a compartment for other components such as drugs or secondary imaging agents. Relaxivity measurements show the relaxivity of [Gd(DhS)]$^-$ in the capsule, [Gd(DhS)]$_{CL}$SLN, to be 7.70 s$^{-1}$mM$^{-1}$, which is significantly higher than that of the parent [Gd(DhS)]$^-$ complex, 4.16 s$^{-1}$ mM$^{-1}$. This is a particularly encouraging result for using this novel SLN system as new nanoscale imaging/therapeutic agents for MRI, fluorescence or drug delivery.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound of formula (I):

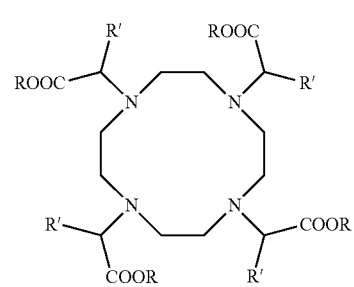

wherein R is H or a cation; R' is mercaptoalkyl or radical of mercaptoalkyl, or alkylthioalkyl.

2. The compound of claim 1, wherein R' is $C_2H_4$—SH, —$C_2H_4$—S., or —$C_2H_4$—S—$CH_3$.

3. The compound of claim 1, wherein R is H, Li$^+$, Na$^+$, K$^+$ or NH$_4^+$.

4. A molecular complex comprising a molecule of formula (III):

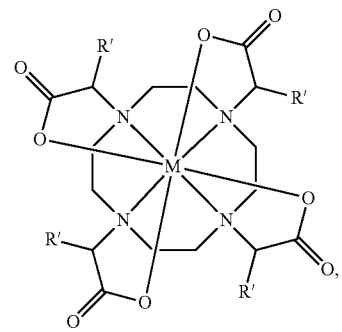

and optionally a balancing counterion, wherein M is a chelating metal ion and R' is a polymer precursor group that is able to self-crosslink or crosslink in presence of one or more crosslinking agents.

5. The molecular complex of claim 4, wherein the metal ion is a lanthanoid.

6. The molecular complex of claim 4, wherein the metal ion is La, Eu, Tb, Gd, Ga, or In.

7. The molecular complex of claim 4, wherein R' is or substituted alkyl group.

8. The molecular complex of claim 4, wherein R' is hydroxyalkyl, mercaptoalkyl or radical of mercaptoalkyl, or alkylthioalkyl.

9. The molecular complex of claim 8, wherein R' is —$CH_2$—OH, —$C_2H_4$—OH, —$C_2H_4$—S—$CH_3$, —$C_2H_4$—SH, or —$C_2H_4$—S.

10. A hyperbranched polymeric nanoparticle or nanocapsule formed from the molecular complex of claim 4.

11. A compound of formula (I):

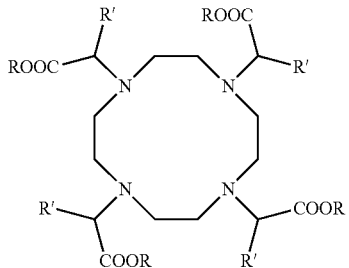

(I)

wherein R is H or a cation; R' is a polymer precursor group which is able to self-crosslink or crosslink in presence of one or more crosslinking agents, and wherein the compounds of formula (I) are chiral.

12. The compound of claim 11, wherein R' is substituted alkyl group.

13. The compound of claim 11, wherein R' is hydroxyalkyl, mercaptoalkyl or radical of mercaptoalkyl, or alkylthioalkyl.

14. The compound of claim 11, wherein R' is —$CH_2$—OH, —$C_2H_4$—OH, —$C_2H_4$—SH, —$C_2H_4$—S., or —$C_2H_4$—S—$CH_3$.

15. The compound of claim 11, wherein R is H, $Li^+$, $Na^+$, $K^+$ or $NH_4^+$.

16. The compound of claim 11, wherein the compound is:

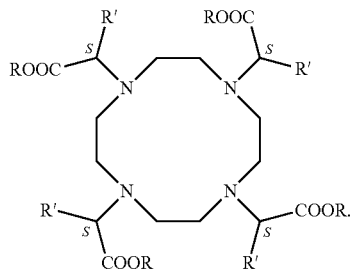

17. A compound of formula (II):

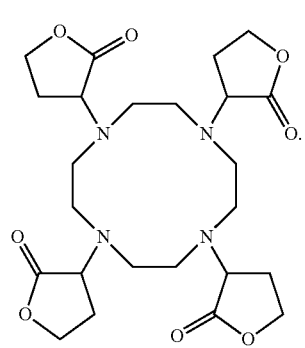

(II)

* * * * *